(12) United States Patent
Ushijima

(10) Patent No.: US 9,050,314 B2
(45) Date of Patent: Jun. 9, 2015

(54) METHODS OF TREATMENT OF ARTHRITIS USING THYMUS-DERIVED COMPOSITIONS

(75) Inventor: Richard N. Ushijima, Wahaiwa, HI (US)

(73) Assignee: CMI Research Management, LLC, Wahaiwa, HI (US)

( * ) Notice: Subject to any disclaimer, the term of this patent is extended or adjusted under 35 U.S.C. 154(b) by 139 days.

(21) Appl. No.: 12/830,181

(22) Filed: Jul. 2, 2010

(65) Prior Publication Data

US 2011/0020465 A1    Jan. 27, 2011

Related U.S. Application Data

(60) Provisional application No. 61/230,529, filed on Jul. 31, 2009, provisional application No. 61/222,636, filed on Jul. 31, 2009, provisional application No. 61/228,709, filed on Jul. 27, 2009.

(51) Int. Cl.
 *A61K 35/26* (2006.01)
 *A61K 36/78* (2006.01)
 *G01N 33/00* (2006.01)

(52) U.S. Cl.
 CPC .............. *A61K 35/26* (2013.01); *A61K 36/78* (2013.01); *G01N 2500/00* (2013.01); *G01N 33/0098* (2013.01)

(58) Field of Classification Search
 None
 See application file for complete search history.

(56) References Cited

U.S. PATENT DOCUMENTS

| | | | |
|---|---|---|---|
| 4,120,951 A * | 10/1978 | Goldstein | 514/9.7 |
| 4,826,680 A | 5/1989 | Jaeger | |
| 5,792,476 A * | 8/1998 | Hallgren | 424/465 |
| 2011/0020464 A1 | 1/2011 | Ushijima | |

FOREIGN PATENT DOCUMENTS

| | | |
|---|---|---|
| WO | WO 9117182 A1 * | 11/1991 |
| WO | WO 2011/016937 | 2/2011 |

OTHER PUBLICATIONS

Sundal et al., Thymopentin Treatment of Rheumatoid Arthritis, 1994, Arzneim.-Forsch. 44(11): 1145-1149.*
Punzi et al., Clinical Significance of Cytokine Determination in Synovial Fluid, 2002, Crit. Rev. Clin. Lab. Sci. 39(1): 63-88.*
Besedovsky et al., Immunoregulatory Feedback Between Interleukin-1 and Glucocorticoid Hormones, 1986, Science 233(4764): 652-654.*
Lu et al., Anti-inflammatory effect of *Houttuynia cordata* injection, 2006, J. Ethnopharmacol. 104(1-2): 245-9.*
Poutsiaka et al., Cross-linking of the beta-Glucan Receptor on Human Monocytes Results in Interleukin-1 Receptor Antagonist But Not Interleukin-1 Production, 1993, Blood 82(12): 3695-3700.*
Malaise et al., Thymopoietin and thymopentin enhance the levels of ACTH, β-endorphin and β-lipotropin from rat pituitary cells in vitro, 1987, Acta Endocrinol. 115: 455-460.*
Bagley, Weak Calf Syndrome or BVD Fetal Infection, 1997, Utah State University, Animal Health Fact Sheet.*
Goldstein et al., A synthetic pentapeptide with biological activity characteristic of the thymic hormone thymopoietin, 1979, Science 204(4399): 1309-1310.*
Malaise et al., Treatment of active rheumatoid arthritis with slow intravenous injections of thymopentin: a double-blind placebo-controlled randomised study, 1985, The Lancet 325(8433): 832-836.*
Bergesi et al., "Caratterizzazione chimica e attivita biologica di un nuovo estratto timico," Folia Allergol. Immunol. Clin., 1977, p. 204-208, vol. 24.
Goldstein et al., "Thymosin and Other Thymic Hormones: Their Nature and Roles in Thymic Dependency of Immunological Phenomena," *Contemporary Topics in Immunobiology*, vol. 2 (Thymus Dependency), Davis/Carter (editors), 1973, Plenum Press, New York, p. 339-350.
Hayashi et al., "Virucidal Effects of the Steam Distillate from *Houttuynia cordata* and its Components on HSV-1, Influenza Virus, and HIV," Planta Med., 1995, pp. 237-241, vol. 61.
Hooper et al., "Purification and Properties of Bovine Thymosin," Annals of the New York Academy of Sciences, 1975, p. 125-144, vol. 249.
Hu et al., "Treatment of Bovine Mastitis with Houttuynin Sodium Bisulphate," Journal of Veterinary Medicine, 1977, pp. 365-370, vol. 44.
Huang, "Yu Xing Cao," *The Pharmacology of Chinese Herbs*, Second Edition, CRC Press, 1999, pp. 392-393.
Ohno et al., "Antitumor 1,3-β-Glucan from Cultured Fruit Body of *Sparassis crispa*," Biol. Pharm. Bull., 2000, pp. 866-872, vol. 23.
Pal et al., "How is Gout Managed in Primary Care? A Review of Current Practice and Proposed Guidelines," Clinical Rheumatology, 2000, pp. 21-25, vol. 19.
Rindsleisch et al., "Diagnosis and Management of Rheumatoid Arthritis," American Family Physician, 2005, pp. 1037-1047, vol. 72.
Terkeltaub, "Gout," New England Journal of Medicine, 2003, pp. 1647-1655, vol. 349.
U.S. Appl. No. 61/222,636, filed Jul. 31, 2009, , entitled "Methods of Treatment of Gout Using Thymus-Derived Compositions," first inventor Ushijima.
U.S. Appl. No. 61/228,709, filed Jul. 27, 2009, entitled "Methods for Treatment of Cancer Using Thymus-Derived Compositions," first inventor Ushijima.
U.S. Appl. No. 61/230,529, filed Jul. 31, 2009, entitled "Methods of Treatment Using Thymus-Derived Compounds," first inventor Ushijima.

* cited by examiner

*Primary Examiner* — Robert Yamasaki
(74) *Attorney, Agent, or Firm* — Davis Wright Tremaine, LLP; Barry L. Davison

(57) ABSTRACT

Embodiments of the present invention provide processes for preparing thymus extracts and plant or fungal extracts, and more particularly provide compositions (Thyex-1-6A and -6B) produced in accordance with said processes, and methods for treatment of various conditions comprising administration of said compositions including but not limited to arthritis and/or arthritis-related conditions, including: gout, rheumatoid arthritis (RA), osteoarthritis (OA), and pseudo-gout, and/or inflammation resulting from any of the conditions Additional aspects provide methods for combination or adjunctive therapies (with anti-inflammatories, etc.). Methods to modulate immune response are also encompassed.

18 Claims, 5 Drawing Sheets

METHODS OF TREATMENT OF ARTHRITIS USING THYMUS-DERIVED COMPOSITIONS

CROSS-REFERENCE TO RELATED APPLICATIONS

This application claims the benefit of priority to U.S. Provisional Patent Application Ser. Nos. 61/230,529, filed 31 Jul. 2009, entitled "Methods of Treatment Using Thymus-Derived Compositions"; 61/222,636, filed 31 Jul. 2009; entitled "Methods of Treatment of Gout Using Thymus-Derived Compositions"; and 61/228,709, filed 27 Jul. 2009, entitled "Methods for Treatment of Cancer Using Thymus-Derived Compositions", incorporated herein by reference in their entirety. In addition, this application is related to the following patent applications: U.S. patent application Ser. No. 12/829,829 (published as US-2011-0020464-A1) and International Application number PCT/US2010/040993 (published as WO 2011/016937) which are incorporated herein by reference in their entirety.

TECHNICAL FIELD OF THE INVENTION

Aspects of the present invention relate to processes for preparing thymus extracts and plant or fungal extracts, and more particularly provide compositions (Thyex-1-Thyex 6A and Thyex-6B) produced in accordance with said processes, and methods comprising administration of said compositions for modulating the immune system and for treatment of various conditions including but not limited to arthritis and/or arthritis-related disorders (e.g, gout, rheumatoid arthritis (RA), osteoarthritis (OA), and pseudogout, and/or inflammation resulting from any of the conditions). Combination or adjunctive therapies (with anti-inflammatories, etc.) are also encompassed.

BACKGROUND

Rheumatic diseases, such as arthritis, are characterized by inflammation and loss of function in one or more connecting or supporting structures of the body. Those structures, in particular, include: joints, tendons, ligaments, bones and muscles and in some cases internal organs. Some rheumatic diseases are classified as connective tissue disorders and include osteoarthritis, bursitis, spondyloarthropathies, fibromyalgia, gout, pseudogout, polymyositis, and tendonitis. Other rheumatic diseases are classified as autoimmune diseases including rheumatoid arthritis, systemic lupus erythematosus, polymyalgia rheumatica, scleroderma, and psoriatic arthritis. While the pathogenesis of the diseases may vary, their characteristic inflammatory symptoms often share common inflammatory mediators.

Arthritis, the most common form of rheumatic diseases, is a group of diseases and disorders that afflict approximately 1% of the world's population. Arthritis is characterized by chronic inflammation of the joint, accompanied by pain, swelling and limitation of movement in joints and connective tissue. It afflicts more than 45 million people in the United States and is the leading cause of disability among adults age 65 and older. The most prevalent forms of arthritis are osteoarthritis and rheumatoid arthritis, both of them are progressive, degenerative diseases that lead to varying degrees of disability. The cartilage and bone of the joint undergo destruction with the progress of the disease, followed by loss of mobility, and increased suffering caused, among others, by the rubbing of bone against bone.

Osteoarthritis. Osteoarthritis (OA) is characterized by degradation of joints, including cartilage and bone. Symptoms include joint pain, stiffness, inflammation, tenderness and locking of joints. Nearly 27 million people in the United States are affected by OA with about a quarter of visits to primary care and 50% of all Non-Steroid Anti-Inflammatory prescriptions due to pain and lowered mobility from OA complications. Two types of osteoarthritis have been described, primary and secondary. Primary osteoarthritis is where the arthritis does not result from some other disorder, infection, or disease. Secondary osteoarthritis is where the arthritis is the result of another disorder, infection, or diseases, like diabetes, inflammatory diseases or hormonal disorders.

Rheumatoid arthritis. Rheumatoid arthritis (RA) is a rheumatic disease characterized by persistent synovial tissue inflammation. In time, this persistent inflammation can lead to bone erosion, destruction of cartilage, and complete loss of joint integrity. Eventually, multiple organs may be affected (Rindfleish et al. American Family Physician (2005), 72(6): 103746). Joint damage is initiated by proliferation of synovial macrophages and fibroblasts after a triggering incident (for example, an autoimmune reaction or an infection). This is followed by infiltration of the perivascular regions by lymphocytes and endothelial cell proliferation, which leads to invasive tissue forming, growing irregularly and eventually invading and destroying cartilage and bone. The symptoms of rheumatoid arthritis include pain and stiffness affecting multiple joints. Symptoms can emerge over weeks and are often accompanied by anorexia, weakness, or fatigue. Joints most commonly affected are those with the highest ratio of synovium to articular cartilage, including the wrist and finger joints (Ruddy et al. eds. Kelly's Textbook of Rheumatology 7.sup.th ed. Philadelphia: W. B. Saunders, 2005:996-1042).

Gout. Gout is a form of acute arthritis, in which suffers have severe pain and swelling in joints. Gout often affects the heel, ankle, hand, wrist, elbow or big toe, and typically has a sudden onset. The symptoms of gout are characterized by the deposition of urate crystals in joint tissues as a result of urate supersaturation of extracellular fluids, a biochemical aberration reflected by hyperuricemia. Initially, however, patients suffer from asymptomatic hyperuricemia, meaning that these patients have elevated serum urate levels in their blood for a period of time before having their first gout attack. An acute attack of gout is manifested by a highly inflammatory arthritis that is often accompanied by intense swelling, redness and warmth surrounding a joint caused by the movement of monosodium urate crystals in or out of the cell. In addition, chills, a low grade fever and an elevated white blood cell count can occur, mimicking an infection. These acute attacks of gout are also referred to as "gout flares". After an initial attack, a patient may go for a period of months or years without or between gout attacks. After a number of years of gouty attacks, patients may develop a chronic arthritis that results in bone and cartilage destruction and deformity. Urate crystals deposit within and surrounding the joint thereby causing a chronic destructive inflammatory process.

It is among the most common causes of acute monoarticular arthritis. In fact, estimates are that gout affects as many as 5 million Americans—twice the number of those affected with rheumatoid arthritis. While it is estimated that the overall incidence of gout among men and women is less than 1% (Pal, B., et al., Clin. Rheumatol., 19:21-25 (2000), Terkeltaub, R. A., N. Engl. J. Med., 349(17):1647-1655 (2003)), white males carry the major burden of this disease with a 8.6% cumulative incidence. (Roubenoff, R., et al., JAMA, 266: 3004-3007 (1991)) In addition to gender, genetics also play a role in gout risk. Specifically, in the U.S., familial incidence of gout ranges from 6 to 18%. (Porter, R., Bull Hist. Med., 68:1-28 (1994)). Among hyperuricemic relatives of gout patients, the incidence of gout averages 20%. (Smyth, C. J., Metabolism, 6:218-229 (1957)).

Pseudogout. Pseudogout is similar in disease manifestation as gout, but it is not a hyperuremic disorder. Instead pseudogout involves the deposition of calcium pyrophosphate. Approximately 50% of the United States population above the age of 85 are affected by pseudogout.

Current treatments for arthritis (including: gout, RA, OA, and pseudogout) are colchicine, anti-inflammatory drugs, and glucocorticoids. The most effective of these, colchicine administered orally, cannot be tolerated by 80 percent of people because of side effects. There is a pronounced need in the art for economically-viable treatments for arthritis.

SUMMARY OF THE INVENTION

Particular embodiments of the present invention provide inventive methods for preparing thymus extracts (Thyex-1-6A and -6B; see working EXAMPLES 1-8), and therapeutic compositions comprising said Thyex preparations.

Additional exemplary embodiments provide methods for treating at least one condition selected from the group consisting of arthritis and related conditions (EXAMPLES 9-16), especially gout related disorders (EXAMPLES 9 and 11), osteoarthritis (EXAMPLE 12), rheumatoid arthritis (EXAMPLE 13), and pseudogout (EXAMPLE 14); and also (allergy- and autoimmune disorders (e.g., lichen sclerosis set atrophicus, rheumatoid arthritis, psoriasis, progressive systematic scleroderma, lupus, and juvenile diabetes), and— inflammation (EXAMPLE 16), comprising administration of a Thyex composition as described herein.

Specifically, particular embodiments of the present invention provide methods for preparing thymus extract compositions (Thyex-1-6A and -6B; EXAMPLES 1-8) for the treatment of impaired physical vigor and stamina, and age related disorders, comprising: homogenizing thymus tissue; removing tissue debris therefrom to produce a supernatant; and concentrating and denaturing the supernatant to produce a clarified supernatant fraction. Preferably, the processes comprise further clarifying of the clarified supernatant by high-speed centrifugation at about 8,500 (g). Preferably the processes further comprise filter sterilizing. Preferably, the pH and ionic strength of the resulting supernatant are physiologically compatible. Preferably, the pH and ionic strength of the resulting supernatant have values of about 7 and of about 0.85% (w/v), respectively. Preferably, the initial ratio of thymus tissue to aqueous homogenization fluid is about 350 g wet weight of thymus tissue to about 0.7 L of homogenization fluid. Preferably, the processes comprise further fractionating based on molecular weight to obtain a final fraction having proteins of about 3.5 to about 30 kDa.

Additional embodiments provide processes for preparing thymus extract compositions for the treatment of impaired physical vigor and stamina, and age related disorders, comprising: homogenizing thymus tissue; removing tissue debris therefrom to produce a supernatant; concentrating, denaturing, and clarifying the supernatant fraction; further concentrating the clarified supernatant fraction to produce a further concentrated fraction; fractionating the further concentrated fraction to remove molecules having a molecular weight less than about 3.5 kDa; and further fractionating based on molecular weight to obtain a final fraction having proteins of about 3.5 to about 30 kDa. Preferably, the processes further comprise adjusting the pH and/or ionic strength, of the final fraction to a physiological or therapeutically compatible value. Preferably, said adjusting is achieved by adding phosphate buffer and/or sodium chloride to produce a solution having a pH value of about 7, and/or an ionic strength of about 0.85% (w/v). Preferably the processes further comprise filter sterilizing. Preferably, said sterilizing is achieved by using a 0.2 μm membrane filter. Preferably, the initial ratio of thymus tissue to aqueous homogenization fluid is about 350 g wet weight (about 400 ml) of thymus tissue to about 0.7 L of homogenization fluid.

Further embodiments provide pharmaceutical compositions for the treatment of arthritis and arthritis related disorders, including: gout, OA, RA, and pseudogout, comprising: thymus extract compositions (Thyex-1-6A and -6B) produced in accordance with the above-described processes, and a pharmaceutically acceptable carrier.

Yet further embodiments provide methods for treating arthritis and arthritis related disorders, including: gout, OA, RA, and pseudogout, comprising: administering of a therapeutically effective amount of a thymus extract composition (Thyex-1-6A and -6B) produced in accordance with the above-described processes. Preferably, the thymus extract composition is administered in combination with administration of macrophage stimulating agent.

DETAILED DESCRIPTION OF THE INVENTION

Figure 1:
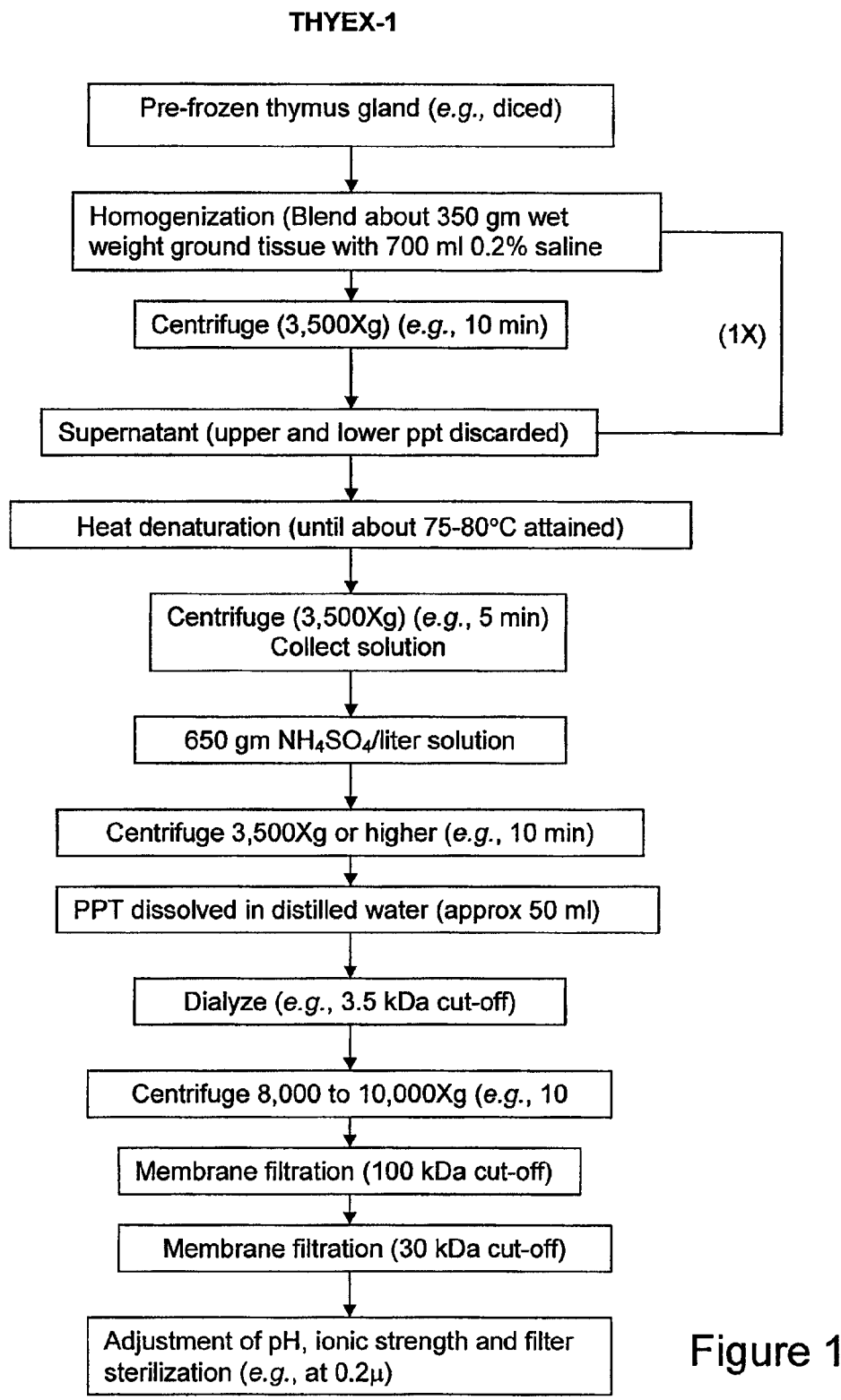
FIG. 1 is a flow diagrammatic representation comprising an inventive Thyex-1 process embodiment for preparing a thymus extract composition.
Figure 2:
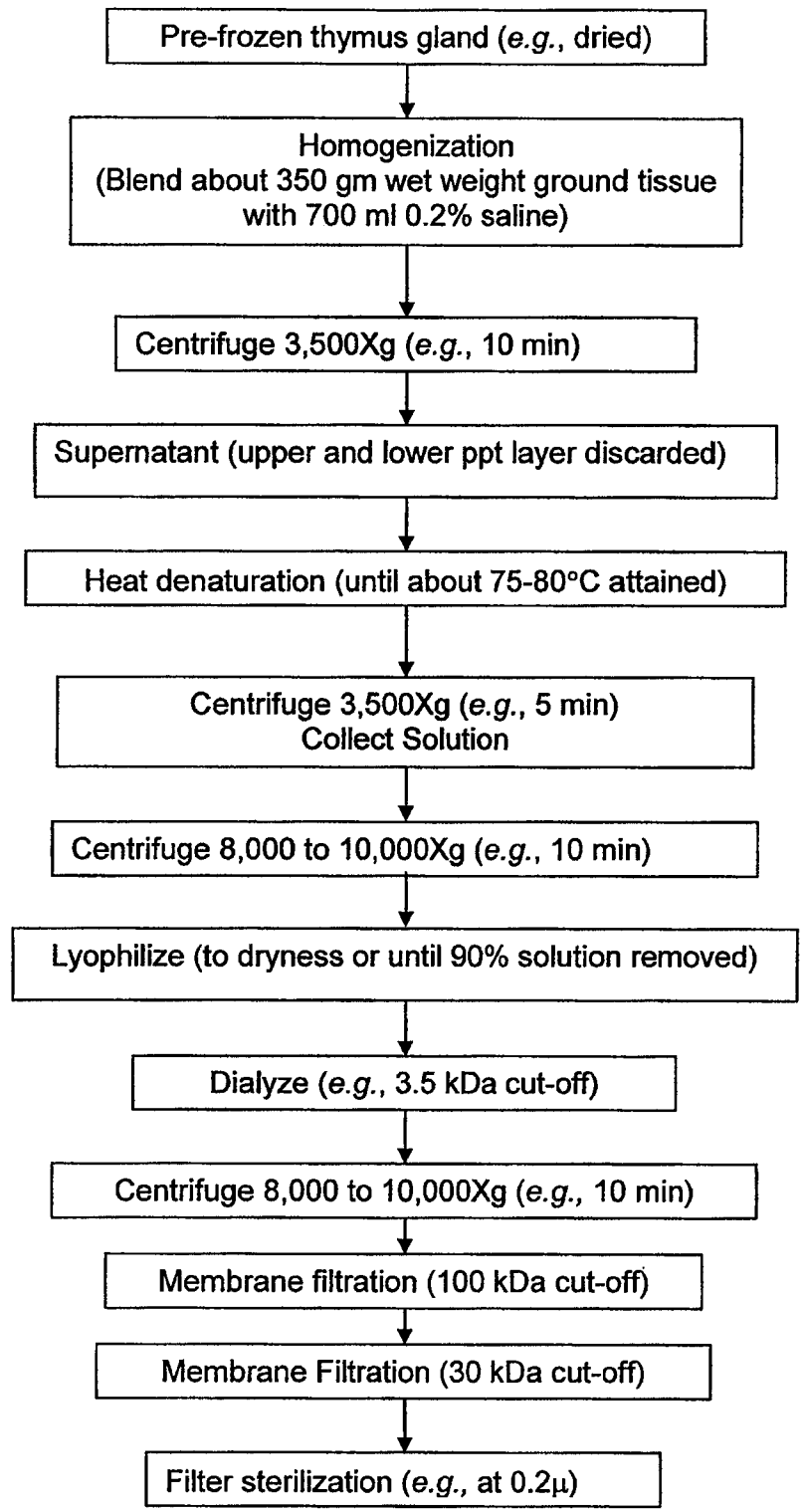
FIG. 2 is a flow diagrammatic representation comprising an inventive Thyex-2 process embodiment for preparing a thymus extract composition.
Figure 3:
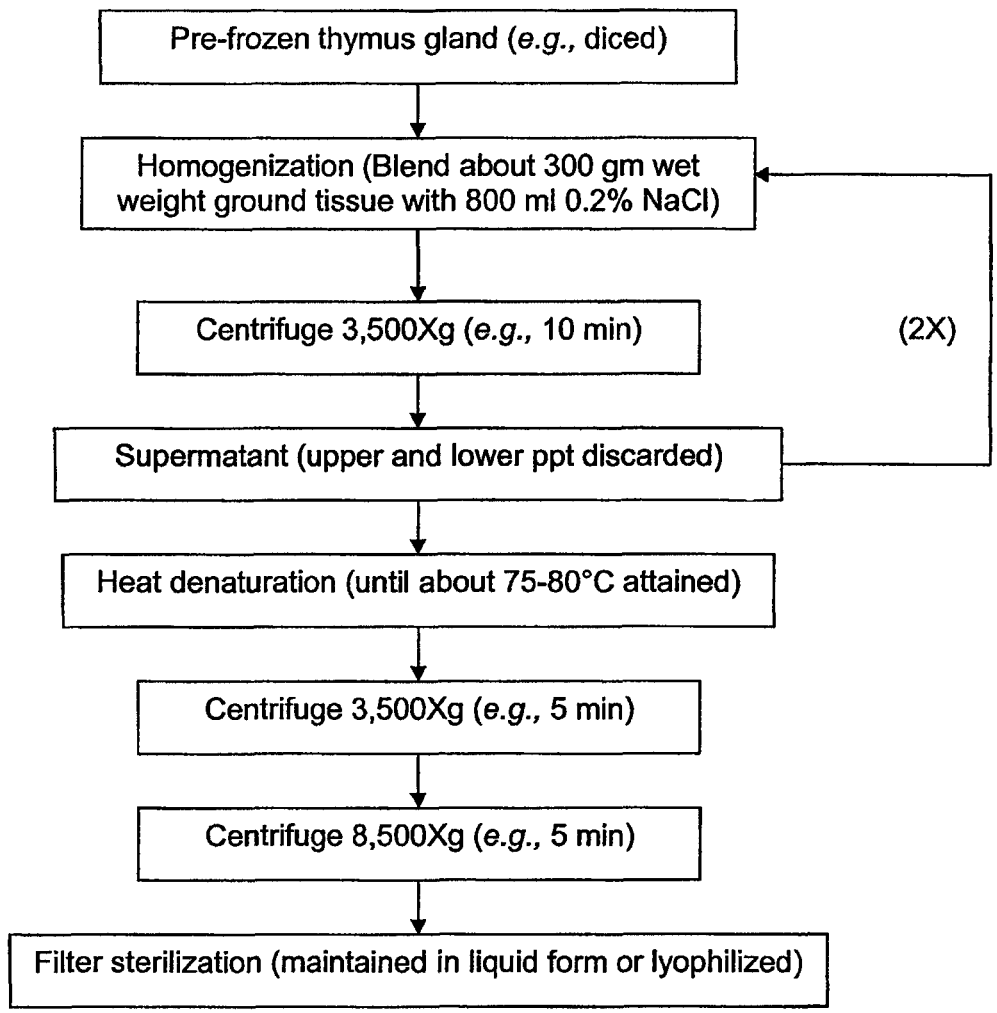
FIG. 3 is a flow diagrammatic representation comprising an inventive Thyex-3 process embodiment for preparing a thymus extract composition.

Aspects of the present invention relate to processes for preparing thymus extracts and plant or fungal extracts, and more particularly provide compositions (Thyex-1-6A and -6B) produced in accordance with said processes, and administration of said compositions in methods for treatment of at least one condition selected from the group consisting of osteoarthritis, bursitis, spondyloarthropathies, fibromyalgia, gout, pseudogout, polymyositis, tendonitis, rheumatoid arthritis, systemic lupus erythematosus, polymyalgia rheumatica, scleroderma, and psoriatic arthritis and/or inflammation resulting from any of the conditions.

In particular aspects, administration of said compositions is used for treatment of gout, rheumatoid arthritis (RA), osteoarthritis (OA), and pseudogout, and/or inflammation resulting from any of the conditions.

In preferred aspects, the inventive compositions (Thyex-1-6A and -6B) are administered in combination with a macrophage stimulating agent.

Particular aspects provide a method for preparing heat-treated, fractionated thymus extract composition, comprising: homogenizing thymus tissue with aqueous homogenization fluid to produce an aqueous thymus homogenate;

removing tissue debris from the aqueous thymus homogenate to produce a primary supernatant; heat denaturing the primary supernatant, and clarifying the denatured primary supernatant by use of at least one of low-speed centrifugation and filtration, to produce a clarified supernatant; and separating molecules having molecular weights less than about 3.5 kDa from the clarified supernatant, wherein a heat-treated, fractionated thymus extract composition lacking proteins or polypeptides having molecular weights less than about 3.5 kDa is provided. In certain aspects, the method further comprises separating molecules having molecular weights greater than about 30 kDa from the heat-treated, fractionated thymus extract composition, wherein a heat-treated, fractionated thymus extract composition comprising proteins or polypeptides having molecular weights in the range of about 3.5 kDa to about 30 kDa is provided. In certain embodiments, the method comprises further clarifying of the clarified supernatant by high-speed centrifugation to produce a final clarified supernatant fraction, and optionally sterilizing the final clarified supernatant fraction to produce a sterile final clarified supernatant fraction. In certain aspects, sterilizing is achieved by passing the final clarified supernatant fraction through a membrane filter. In particular embodiments, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. In certain aspects, heat denaturing and clarifying of the primary supernatant is achieved by heat denaturation, followed by low-speed centrifugation and crude filtration to remove particulate matter. In certain embodiments, the methods further comprise lyophilization of the final clarified supernatant fraction. Preferably no steps involving exogenously added protease digestion, or extraction with organic solvents are used.

Additional particular aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; heat denaturing the primary supernatant, and clarifying the denatured primary supernatant by use of at least one of low-speed centrifugation and filtration to produce an intermediate clarified supernatant; concentrating the intermediate clarified supernatant to produce a concentrated intermediate fraction; and separating molecules having molecular weights less than about 3.5 kDa from the concentrated intermediate fraction, wherein a heat-treated, fractionated thymus extract composition lacking proteins or polypeptides having molecular weights less than about 3.5 kDa is provided. In certain embodiments, the method further comprises separating molecules having molecular weights greater than about 30 kDa from the heat-treated, fractionated thymus extract composition, wherein a heat-treated, fractionated thymus extract composition comprising proteins or polypeptides having molecular weights in the range of about 3.5 kDa to about 30 kDa is provided. Certain embodiment further comprise clarifying of the concentrated intermediate fraction by high-speed centrifugation to produce a final clarified supernatant fraction. Particular aspects further comprise adjusting at least one of the pH or ionic strength of the fraction having proteins or polypeptides of molecular weight of about 3.5 to about 30 kDa to a physiological or therapeutically compatible value, to produce a pH- or ionic strength-adjusted fraction, and in certain aspects, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. Certain embodiments further comprise sterilizing the pH-, or ionic strength-adjusted fraction to produce a sterile pH-, or ionic strength-adjusted fraction, and in particular aspects, sterilizing is achieved by passing the fraction through a membrane filter. In particular embodiments, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. For particular embodiments, heat denaturing and clarifying of the primary supernatant is achieved by heat denaturation, followed by low-speed centrifugation and crude filtration to remove particulate matter. In particular embodiments, concentrating the intermediate supernatant involves concentrating and fractionating, wherein the concentrating and fractionating is achieved by adding ammonium sulfate to the intermediate clarified supernatant, followed by low-speed centrifugation and suspension of the resulting ammonium sulfate pellet in an aqueous solution to provide a concentrated intermediate fraction. In particular aspects, separating molecules having molecular weights less than about 3.5 kDa from the concentrated intermediate fraction comprises dialysis of the concentrated intermediate fraction, followed by high-speed centrifugation to remove particulate matter, to provide for a clarified concentrated intermediate fraction lacking proteins or polypeptides having molecular weights less than about 3.5 kDa. In certain embodiments, separating molecules having molecular weights greater than about 30 kDa from the heat-treated, fractionated thymus extract composition, is achieved by passing the clarified concentrated intermediate fraction lacking proteins or polypeptides having molecular weights less than about 3.5 kDa consecutively through a first and a second membrane filter having exclusion limits of about 100 and about 30 kDa, respectively, and collecting the filtrate. Particular aspects further comprise lyophilization of the heat-treated, fractionated thymus extract composition comprising proteins or polypeptides having molecular weights in the range of about 3.5 kDa to about 30 kDa.

Yet additional particular aspects provide a composition or pharmaceutical composition, comprising a thymus extract composition produced in accordance with the methods recited herein.

Additional aspects provide an inflammation reducing agent, comprising a thymus extract composition produced in accordance with the methods recited herein. In certain embodiments, the supplement comprises an anti-inflammatory component for use in combating inflammation.

Additional aspects provide a method for treating arthritis or arthritis-related symptom or condition, comprising administering to a mammalian subject in need thereof a therapeutically effective amount of a thymus extract composition produced in accordance with the methods recited herein, wherein at least one arthritis-related symptom or condition is treated or alleviated. In certain aspects the mammal is a human. In particular aspects, the arthritis-related condition is at least one selected from the group consisting of arthritis, mobility deficits, gout, rheumatoid arthritis (RA), osteoarthritis (OA), and pseudogout, and/or inflammation resulting from any of the conditions.

Further aspects provide a method for immuno stimulation or immunoregulation, comprising administering to a mammalian subject in need thereof a therapeutically effective amount of a thymus extract composition produced in accordance with the methods recited herein, wherein at least one of immuno stimulation or immunoregulation is afforded.

Definitions:

"Thymus extract" or thymus extract composition, refers to a composition produced in accordance with one or more of the Thyex-1, -2, -3, -4, -5, -6A and -6B processes disclosed herein.

"Animals" as used herein for treatment of subjects refers to chicken, duck, fish, hamster, rat, guinea pig, human, canine, feline, bovine, equine (e.g., race horse), ovine, goat, and porcine.

"*Houttuynia cordata*" extract refers to a compositions produced in accordance with the on or more of the D-YXC-1 and 2 processes disclosed herein "Anti-microbial agent" means an agent with, for example, antibacterial, antifungal or antiviral activity, including, but not limited to: plant extracts (e.g., *Houttuynia cordata* extracts); antibiotics, such as β-lactam antibiotics, erythromycin compounds, Tetracycline compounds, aminoglycoside antibiotics, cephalosporin compounds, anthracycline compounds, phleomycin group antibiotics, sulfonamide compounds, macrolide antibiotics (e.g., tylosin, desmycosin, macrocin, and lactenocin), quinolone and quinolonyl compounds (e.g., quinolonyl lactams and quinolone thioureas, and carbacephem- and carbapenem-quinolones) carbapenem compounds, along with those antibiotic agents more commonly used in the swine industry, such as lankacidin-group antibiotics and derivatives, diterpene antibiotics (e.g, tiamulin-type), polyether or polycyclic ether antibiotics and derivatives (e.g., A82810), lysocellin, treponemycin, antibiotic 10381b, antibiotics GE 37468 A, B and C, A41030 antibiotics, antibiotic A47934, antibiotic BN-109, apramycin, actaplanin antibiotics, antibiotic A3823, antibiotic X-14766A, dihydromocimycin antibiotics, BM123γ-type antibiotics, antibiotic AV290, antibiotic A-32887, glycopeptide antibiotic UK-68,597, valnemulin, tiamulin, oxytetracyclin, chlortetracycline, tylosin, and manganese-containing antibiotic agents, copper-containing bleomycin group antibiotics; antifungal agents, such as partanamicins, fusacandins; and antihelminthic agents such as spiroketals, avermectin and milbemycin; and combinations thereof.

"Crude filtration" or "coarse filtration" means filtering a solution having particulate, precipitated or flocculent suspended material through, e.g., one or more layers of standard cheese cloth, or other sieving device (e.g., screen, strainer, colander, etc.), to remove said material.

"Low-speed centrifugation" means centrifugation at about 3,500×g (±5% or ±10%) for about 5-10 minutes (±5% or ±10%), or an equivalent sedimentation protocol thereof.

"High-speed centrifugation" means centrifugation at about 8,500×g (±5% or ±10%) for about 10 minutes (±5% or ±10%), or the equivalent sedimentation protocol thereof.

"Clarifying," or clarification of a supernatant fraction means removing particulate matter (e.g., precipitates, bacteria) from a solution containing such particulate matter through the use of standard separation techniques, such as low- or high-speed centrifugation (as defined above) or filtration.

With respect to fractionation of the particular supernatant fractions, the phrase "less than about 3.5 kDa" as used herein refers to less than 3.5 kDa, or less than a molecular weight that varies by ±5% or ±10% therefrom. Similarly, the phrase "proteins or polypeptides of molecular weight of about 3.5 to about 30 kDa" as used herein refers to proteins or polypeptides in a molecular weight ranged from 3.5 kDa, or from a molecular weight that varies by ±5% or ±10% therefrom, to 30 kDa, or to a molecular weight that varies by ±5% or ±10% therefrom.

With respect to pH and ionic strength, the phrase "a pH value of about 7, or an ionic strength of about 0.85% w/v." as used herein refers to a pH of 7 or a pH that varies by ±5% or ±10% therefrom, and/or an ionic strength of 0.85% w/v, or an ionic strength that varies by ±5% or ±10% therefrom.

"Vaccine" is defined herein in its broad sense to refer to any type of biological agent, administrable for the purpose of priming, enabling or enhancing an immune response against in an animal inoculated with the vaccine.

"Unpalatable," as used herein, refers to the art-recognized off-putting and/or bitter flavor widely recognized in the context of *Houttuynia cordata* extract. For example, those familiar with *Houttuynia cordata* extract (e.g., tea) described it as being bitter and/or fishy and that this flavor renders the extract largely unpalatable. The disclosed invention not only provides for separation of the unpalatable and palatable portions but also allows for separation of the anti-nausea and/or anti-emetic activity from the largely unpalatable portion using the heat-distilled technique as herein disclosed. The term "separation," as used herein can mean either separation of the unpalatable taste from the palatable taste in particular embodiments, or in alternate embodiments can mean loss of the unpalatable taste. "Unpalatable", as used herein, refers in particular embodiments to the non-heat-distilled *Houttuynia cordata* extract (e.g., the aqueous extract and the separated aqueous extract) being unpleasant, inedible, indigestible, disgusting, revolting, foul-tasting, nasty, bad, distasteful, disagreeable, bitter, offensive, unattractive, horrid, unsavory, displeasing, and repugnant.

"Bitter" and "bitterness," as used herein, refers in particular embodiments to the flavor the non-heat-distilled *Houttuynia cordata* extract (e.g., the aqueous extract and the separated aqueous extract). In particular, bitter refers to being or inducing the one of the four basic taste sensations that is particularly acrid, astringent, or disagreeable and suggestive of an infusion of hops.

"Substantially non-bitter," as used herein, refers in particular embodiments to reducing the bitterness/foulness of the extract by approximately half of the original non-heat-distilled *Houttuynia cordata* extract (e.g., the aqueous extract and the separated aqueous extract) or by reducing the bitterness/foulness to such a level that one would reasonably regard the solution as being palatable and/or without a unpleasant, inedible, indigestible, disgusting, revolting, foul-tasting, nasty, bad, distasteful, disagreeable, bitter, offensive, unattractive, horrid, unsavory, displeasing, and repugnant flavor. "Substantially non-bitter," as used herein, refers in particular embodiments to reducing the bitterness/foulness of the extract by approximately 60%. Preferably, particular embodiments relate to reducing the bitterness/foulness of the extract by approximately 70%. More preferably, particular embodiments relate to reducing the bitterness/foulness of the extract by approximately 75%. Even more preferably, particular embodiments relate to reducing the bitterness/foulness of the extract by approximately 80%. Still more preferably, particular embodiments relate to reducing the bitterness/foulness of the extract by approximately 85%. Most preferably, particular embodiments relate to reducing the bitterness/foulness of the extract by approximately 90%.

Methods for Preparing Thymus Extracts:

Particular embodiments of the present invention (see working EXAMPLES 1-8) provide novel processes for preparing therapeutically useful extracts (Thyex-1-6A and -6B) of thymus tissue. In particular aspects, the inventive processes are readily distinguishable from other known processes for preparing thymus extracts (e.g., Goldstein & White, Contemp. Topics in Immunobiology, p 339, 1973; Bergesi et al., *Folia Allergol. Immunol. Clin.* 21:201, 1977; Hooper et al., "The purification and properties of bovine thymosin," *Ann. NY Acad. Sci.* 249:125, 1975; U.S. Pat. No. 4,826,680, issued 2 May 1989 to Jaeger, Pharmaceutical Composition Containing Thymus Extract Fractions), and lack steps involving decalcite ($CaCO_3$) treatment, protease digestion, extraction with organic solvents (e.g., phenol, acetone or ethanol) or fractionation by column chromatography. Not only are the inventive compositions surprisingly effective in view of the teachings of the art, but the compositions produced in accordance with the instant processes are also further distinguished from those of the prior art by the molecular weight ranges of their protein elements.

The instant processes comprise steps to optimize protein compositions for therapeutic use of. For example, particular of the below-described process embodiments (Thyex-1-6A and -6B) are designed to provide therapeutic compositions, and include ammonium sulfate precipitation/fractionation and/or lyophilization steps, respectively, to facilitate optimal protein concentration and fractionation. The Thyex-3 process embodiment lacks an ammonium sulfate or lyophilization step, but provides for a sufficiently-concentrated composition by reusing (and thereby augmenting) an initial tissue homogenization supernatant fraction as homogenization fluid to homogenize additional tissue. The resulting Thyex-3 composition is less refined relative to those of Thyex-1 and Thyex-2, but is nonetheless suitably concentrated and formulated for efficacious delivery. The Thyex 6A and Thyex 6B process embodiments described below are designed to provide therapeutic compositions suitable for delivery as a topical ointment or by injection or inhalation, and include ammonium sulfate precipitation/fractionation steps. Thyex 5 is prepared from a similar process but is less refined (less fractionated) than Thyex 6A or Thyex 6B and is optimally mixed with an amount of an extracted lyophilized herbal source composition, and administered orally in filled gelatin capsules. The Thyex 4 process embodiment lacks ammonium sulfate precipitation step but comprises lyophilization to provide for a sufficiently-concentrated composition. The resulting Thyex 4 composition is less refined in relative to those of Thyex 5 or Thyex 6A or 6B, but is nonetheless suitably concentrated and formulated for efficacious oral deliver in both animals and humans.

Figure 4:
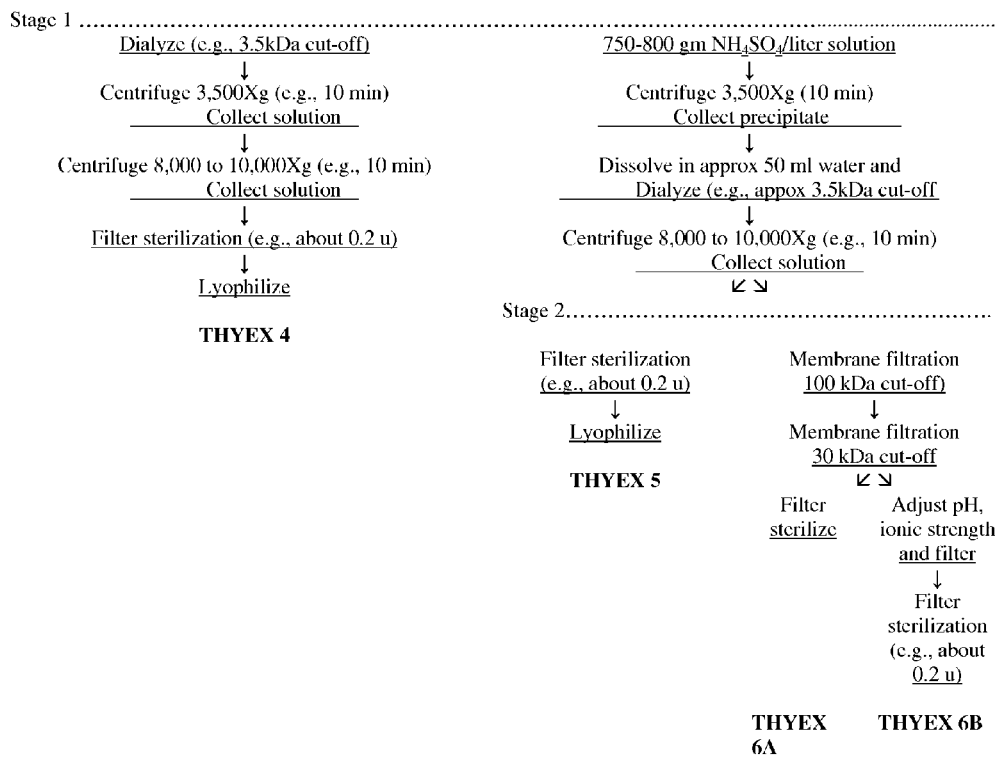
FIG. 4 is a flow diagrammatic representation comprising an inventive Thyex-4, -5 and -6 process embodiments for preparing a thymus extract composition.

Preferably, the thymus preparations are those comprising Thyex-4,5-, -6A and -6B (see FIG. 4, and EXAMPLES 4-8).

Particular specific aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; and heat denaturing and clarifying the primary supernatant to produce a clarified supernatant. In certain aspects, the method further comprises further clarifying of the clarified supernatant by high-speed centrifugation to produce a final clarified supernatant fraction. In certain embodiments, the method further comprises sterilizing the final clarified supernatant fraction to produce a sterile final clarified supernatant fraction. In particular aspects, sterilizing is achieved by passing the final clarified supernatant fraction through a membrane filter. In particular implementations, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. In particular aspects, heat denaturing and clarifying of the primary supernatant is achieved by heat denaturation, followed by low-speed centrifugation and crude filtration to remove particulate matter. In certain implementations, the method further comprises lyophilization of the final clarified supernatant fraction.

Additional aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; heat denaturing and clarifying the primary supernatant to produce an intermediate supernatant; and concentrating the intermediate supernatant to produce a concentrated intermediate fraction. In certain aspects, the method further comprises further clarifying of the concentrated intermediate fraction by high-speed centrifugation to produce a final clarified supernatant fraction. In particular embodiments, the method further comprises fractionating the final clarified supernatant fraction to remove molecules having a molecular weight less than about 3.5 kDa to produce a fractionated intermediate fraction. In certain aspects, the method further comprises fractionating the fractionated intermediate fraction, based on molecular weight, to obtain a fraction having proteins of about 3.5 to about 30 kDa. In particular implementations, the method further comprises adjusting at least one of the pH or ionic strength of the fraction having proteins of about 3.5 to about 30 kDa to a physiological or therapeutically compatible value, to produce a pH- or ionic strength-adjusted fraction. In certain aspects, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. In certain aspects, the method further comprises sterilizing the pH-, or ionic strength-adjusted fraction to produce a sterile pH-, or ionic strength-adjusted fraction. In particular embodiments, sterilizing is achieved by passing the fraction through a membrane filter. In certain aspects, the initial ratio of thymus tissue to aqueous homogenization fluid is about 350 g wet weight of thymus tissue to about 0.7 L of homogenization fluid. In particular embodiments, removing tissue debris from the aqueous thymus homogenate is achieved by a combination of low-speed centrifugation and crude filtration. In certain aspects, heat denaturing and clarifying of the secondary supernatant is achieved by heat denaturation, followed by low-speed centrifugation and crude filtration to remove particulate matter. In particular implementations, concentrating the intermediate supernatant involves concentrating and fractionating, and wherein the concentrating and fractionating is achieved by adding ammonium sulfate to the intermediate supernatant, followed by low-speed centrifugation and suspension of the resulting ammonium sulfate pellet in an aqueous solution. In some embodiments, fractionating the concentrated intermediate fraction to remove molecules having a molecular weight less than about 3.5 kDa is achieved by dialysis of the concentrated intermediate fraction, followed by high-speed centrifugation to remove particulate matter. In particular aspects, fractionating the fractionated intermediate fraction, based on molecular weight, is achieved by passing the fractionated intermediate fraction consecutively through a first and a second membrane filter having exclusion limits of about 100 and about 30 kDa, respectively, and collecting the filtrate. In certain aspects, the method further comprises lyophilization of the fraction having proteins of about 3.5 to about 30 kDa.

Particular specific aspects provide a process for preparing a thymus extract composition, comprising: homogenizing thymus tissue with aqueous homogenization fluid to produce an aqueous thymus homogenate; removing tissue debris from the aqueous thymus homogenate to produce a primary supernatant; concentrating the primary supernatant to produce a secondary supernatant; and denaturing and clarifying the secondary supernatant to produce a clarified supernatant. In certain embodiments, the method further comprises further clarifying of the clarified supernatant by high-speed centrifugation to produce a final clarified supernatant fraction. In particular embodiments, the method further comprises sterilizing the final clarified supernatant fraction to produce a sterile final clarified supernatant fraction. In certain implementations, sterilizing is achieved by passing the final clarified supernatant fraction through a membrane filter. In certain aspects, the initial ratio of thymus tissue to aqueous homogenization fluid is about 300 g wet weight, or about 340 ml wet volume, of thymus tissue to about 0.8 L of homogenization fluid. In certain aspects, removing tissue debris from the aqueous thymus homogenate is achieved by a combination of low-speed centrifugation and crude filtration. In particular embodiments, concentrating the primary supernatant is achieved by repeating (a) and (b) using the primary supernatant, in place of the aqueous homogenization fluid, for homogenizing additional thymus tissue. In certain aspects, denaturing and clarifying of the secondary supernatant is achieved by heat denaturation, followed by low-speed centrifugation and crude filtration to remove particulate matter.

Additional specific aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; concentrating the primary supernatant to produce a secondary supernatant; denaturing and clarifying the secondary supernatant to produce an intermediate supernatant; concentrating the intermediate supernatant to produce a concentrated intermediate fraction; fractionating the concentrated intermediate fraction to remove molecules having a molecular weight less than about 3.5 kDa to produce a fractionated intermediate fraction; and fractionating the fractionated intermediate fraction, based on molecular weight, to obtain a fraction having proteins of about 3.5 to about 30 kDa. In certain embodiments, the method further comprises adjusting at least one of the pH or ionic strength of the fraction having proteins of about 3.5 to about 30 kDa to a physiological or therapeutically compatible value, to produce a pH- or ionic strength-adjusted fraction. In particular implementations, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. In some aspects, the method further comprises sterilizing the pH-, or ionic strength-adjusted fraction to produce a sterile pH-, or ionic strength-adjusted fraction. In particular embodiments, sterilizing is achieved by passing the fraction through a membrane filter. In certain aspects, the initial ratio of thymus tissue to aqueous homogenization fluid is about 350 g wet weight of thymus tissue to about 0.7 L of homogenization fluid. In certain embodiments, removing tissue debris from the aqueous thymus homogenate is achieved by a combination of low-speed centrifugation and crude filtration. In certain aspects, concentrating the primary supernatant is achieved by repeating (a) and (b) using the primary supernatant, in place of the aqueous homogenization fluid, for homogenizing additional thymus tissue. In particular implementations, denaturing and clarifying of the secondary supernatant is achieved by heat denaturation, followed by low-speed centrifugation and crude filtration to remove particulate matter. In particular aspects, the intermediate supernatant is concentrated, wherein concentrating is achieved by lyophilizing the intermediate supernatant either to complete dryness followed by aqueous resuspension to about 500 ml/13.6 kg (30 lbs.) original wet tissue, or to a volume of about 10% of its original volume. In particular aspects, concentrating the intermediate supernatant involves concentrating and fractionating, and wherein the concentrating and fractionating is achieved by adding ammonium sulfate to the intermediate supernatant, followed by low-speed centrifugation and suspension of the resulting ammonium sulfate pellet in an aqueous solution. In certain embodiments, fractionating the concentrated intermediate fraction to remove molecules having a molecular weight less than about 3.5 kDa is achieved by dialysis of the concentrated intermediate fraction, followed by high-speed centrifugation to remove particulate matter. In particular aspects, fractionating the fractionated intermediate fraction, based on molecular weight, is achieved by passing the fractionated intermediate fraction consecutively through a first and a second membrane filter having exclusion limits of about 100 and about 30 kDa, respectively, and collecting the filtrate.

Additional aspects provide a pharmaceutical composition, comprising a thymus extract composition produced in accordance with one or more of the processes disclosed herein.

Methods of Treating:

The term "treating" refers to, and includes, reversing, alleviating, inhibiting the progress of, or preventing a disease, disorder or condition, or one or more symptoms thereof; and "treatment" and "therapeutically" refer to the act of treating, as defined herein.

A "therapeutically effective amount" is any amount of any of the compounds utilized in the course of practicing the invention provided herein that is sufficient to reverse, alleviate, inhibit the progress of, or prevent a disease, disorder or condition, or one or more symptoms thereof.

According to particular aspects the methods comprise administration of a composition comprising at least one of Thyex-1-6A and -6B, as defined herein, in combination with (e.g., adjunctive therapy) administration of a macrophage stimulating agent.

According to particular aspects the methods comprise administration of a composition comprising at least one of Thyex-1-6A and -6B, as defined herein, in combination with (e.g., adjunctive therapy) administration of a macrophage stimulating agent.

According to particular aspects, a polysaccharide is used as preferred macrophage stimulating agent. In preferred aspects, the macrophage stimulating agent comprises a beta glucan. In particular embodiments, the beta glucan comprises at least one linkage selected from the group consisting of beta: 1,3; 1,4; and 1,6 glucan linkages. Preferably, the linkage is that of beta 1,3 glucan.

According to particular aspects the inventive Thyex compositions are used in adjunctive therapies with extracts of at least one of: *Paresis crepe* (aka cauliflower mushroom or hanabaritake) preparations comprising beta 1-3 glucan; *Lentinula edodes* (shitake; e.g., alkaline digest according to the procedure reported by Ohno et al. (Biol. Phar. Bull. 23 866-872, 2000), comprises beta 1-3 glucan and chitin; *Astralagas membranaceus; Scutellaria baicalensis; Lilium longiforum* (aka Easter lily); and *Houttuynia cordata* extracts.

Additional aspects provide a pharmaceutical composition, comprising a thymus extract composition produced in accordance with one or more of the processes disclosed herein.

Combination therapies. Combination therapies are also encompassed by aspects of the present invention. For example, the inventive methods may further comprise administration of a therapeutically effective amount of one or more colchicine, anti-inflammatory drugs, and oral and/or intraarticular glucocorticoids. Anti-inflammatory drugs may include: non-steroidal anti-inflammatory drugs (NSAIDs) (such as COX-2 inhibitors, diclofenac, etoricoxib, indomethacin, ketoprofen, naproxen or sulindac). Glucocorticoids may include: hydrocortisone (cortisol), cortisone acetate, prednisone, prednisolone, methylprednisolone, dexamethasone, betamethasone, triamcinolone, and beclometasone.

Methods for Preparation of *Houttuynia cordata* Extracts:

Additional embodiments of the present invention (see working EXAMPLE 15) provide methods for preparing therapeutic extracts (D-YXC-1 and D-YXC-2) from the medicinal herb *Houttuynia cordata* Thunb. The processes comprise aqueous extraction and distillation steps.

Methods for Treatment of Arthritis and Related Conditions:

According to additional aspects (see working EXAMPLES 9-11), the inventive Thyex compositions have substantial utility for additionally affecting aspects of inflammation, and have utility for treatment of arthritis and related conditions.

Without being bound by mechanism, these observations are explained, at least in part, by reducing inflammation.

According to particular aspects, Thyex directs the immune system to limit inflammatory response and thereby reduces injury to joints caused by arthritis.

Yet further specific exemplary aspects, provide a method for treating arthritis or arthritis-related conditions, comprising administering to a subject in need thereof a therapeutically effective amount of a thymus extract composition produced in accordance with one or more of the processes disclosed herein. In certain embodiments, the arthritis-related condition is at least one selected from the group consisting of arthritis, mobility deficits, gout, rheumatoid arthritis (RA), osteoarthritis (OA), and pseudogout, and/or inflammation resulting from any of the conditions.

Methods for Treatment of Allergy and/or Autoimmune Disease:

According to additional aspects (see working EXAMPLE 16), the inventive Thyex compositions are used to treat individuals with allergy and autoimmune disorders (lichen sclerosis set atrophicus, rheumatoid arthritis, psoriasis, progressive systematic scleroderma, lupus, and juvenile diabetes) and includes reducing inflammation.

Without being bound by theory, the mechanism likely comprises stimulation of suppressor T cells, which direct B cells producing the allergy antibodies to stop continued activity and control of reactive T cells.

Compositions:

Additional embodiments provide compositions produced in accordance with said processes. The Thyex-1, -2, -3, -4, -5, -6A and -6B composition embodiments are produced in accordance with the corresponding Thyex-1-6A and -6B processes (Working EXAMPLES 1-8). Likewise, the D-YXC-1, and 2 composition embodiments are produced in accordance with the corresponding D-YXC-1, and 2 processes (EXAMPLE 15).

Methods of Treatment:

Further embodiments provide methods for the treatment of arthritis, mobility deficits, gout, rheumatoid arthritis (RA), osteoarthritis (OA), and pseudogout, and/or inflammation resulting from any of the conditions, comprising: utilizing thymus extract compositions alone, or in combination with a macrophage stimulating agent (see working EXAMPLE 10 below).

Treatment in Humans with Thyex-1-6A and 6B Compositions, with and without Macrophage Stimulating Agents.

Thyex-1-3 processes. EXAMPLES 1-3 provide exemplary process embodiments used for preparing Thyex-1-3, produced in accordance therewith suitable for oral delivery. Alternatively, Thyex-1-3 are lyophilized, stored at ambient temperature and reconstituted with sterile water prior to use.

Thyex-4 process. Steps (1)-(11) of EXAMPLE 4 comprise a process embodiment for producing Thyex-4 (step (12) relates to storage), suitable for oral delivery. Alternatively, Thyex-4 is lyophilized, stored at ambient temperature and reconstituted with sterile water prior to use.

Thyex-5 process. Steps (1)-(13) EXAMPLE 5 comprise a process embodiment for producing Thyex-5 (step (14) relates to storage), suitable for oral delivery. Alternatively, Thyex-5 is lyophilized, stored at ambient temperature and reconstituted with sterile water prior to use.

Thyex-6A process. EXAMPLE 6 provides an exemplary process embodiment used for preparing Thyex-6A produced in accordance therewith suitable for oral delivery, or delivery as a topical ointment or by injection or inhalation. Alternatively, Thyex-6A is lyophilized, stored at ambient temperature and reconstituted with sterile water prior to use.

Thyex-6B process. EXAMPLE 7 provides an exemplary process embodiment used for preparing Thyex-6B produced in accordance therewith suitable for oral delivery, or delivery as a topical ointment or by injection or inhalation. Alternatively, Thyex-6B was lyophilized, stored at ambient temperature and reconstituted with sterile water prior to use.

Methods for Treatment of Nausea and/or Vomiting Using Heat-Distilled *Houttuynia cordata* Extract.

According to additional aspects (see working EXAMPLES 10 and 17-20), the inventive heat-distilled *Houttuynia cordata* extract is useful in the treatment of nausea and/or vomiting in an affected or susceptible subject in need thereof, comprising administering to the subject a therapeutically-effective amount of a heat-distilled *Houttuynia cordata* extract composition produced in accordance with one or more of the processes disclosed herein. In certain aspects, the method further comprises administering an additional anti-nausea and/or anti-emetic agent in combination with administration of the heat-distilled *Houttuynia cordata* extract composition. In further aspects, the method comprises administering an additional anti-nausea and/or anti-emetic agent sequentially with administration of the heat-distilled *Houttuynia cordata* extract composition. In yet further aspects, the method comprises administering an additional anti-nausea and/or anti-emetic agent at a similar time with administration of the heat-distilled *Houttuynia cordata* extract composition.

According to additional aspects (see working EXAMPLES 10 and 17-20), the inventive heat-distilled *Houttuynia cordata* extract is useful in the treatment of nausea and/or vomiting brought on by any condition including, but not limited to pregnancy (e.g., morning sickness), motion sickness, gastrointestinal obstruction, peptic ulcer, drug toxicity, myocardial infarction, renal failure, and hepatitis. In addition, nausea and/or vomiting can be the side effect of many cancer treatments, including but not limited to chemotherapeutic drugs, radiation, and surgery.

According to further aspects, the inventive heat-distilled *Houttuynia cordata* extract has substantial utility to treat nausea in both humans and animals caused by illnesses, infections, or other treatments, and in particular embodiments is used in combination with one or more of the inventive Thyex compositions, plus or minus standard chemotherapy drugs, for the treatment of cancer.

In further aspects the method further comprises administering the heat-distilled *Houttuynia cordata* extract composition with a standard chemotherapy drugs, for the treatment of cancer. Standard chemotherapeutic drugs are well known in the art. In yet further aspects the method comprises administering the heat-distilled *Houttuynia cordata* extract composition in combination with a chemotherapeutic agent, wherein the administration can occur simultaneously, sequentially, or as needed to relieve nausea and vomiting symptoms.

Dose Determinations

A therapeutically effective dose of a composition of the present invention refers to that amount of the composition sufficient to prevent or inhibit the effects of the treated condition, or to that amount sufficient to enhance the efficacy of adjunctive regimens. This amount may vary somewhat among subjects, but are nonetheless reasonably determined by one of ordinary skill within the art in view of the many art-recognized symptoms associated with the treated conditions.

Therapeutically effective doses of the disclosed compositions are administered alone or in combination with other therapeutic agents, such as macrophage stimulating agents, colchicine, anti-inflammatory drugs, and oral and/or intraarticular glucocorticoids, or are administered as adjunctive therapy in combination with administration of other treatment regimens.

In particular aspects, as in the Examples herein, the Thyex compositions are standardized at a protein concentration about 1 mg/ml. Preferably, the daily dose range for Thyex administration by injection is from about 0.05 mg/kg to about 1 mg/kg. More preferably, the dose range for Thyex administration by injection is from about 0.05 mg/kg to about 0.5 mg/kg. Even more preferably, the dose range for Thyex administration by injection is from about 0.1 mg/kg to about 0.4 mg/kg. Most preferably, the dose range for Thyex administration by injection is from about 0.2 mg/kg to about 0.3 mg/kg.

In particular aspects, the daily dose range for Thyex oral administration is from about 1 mg/kg to about 20 mg/kg. More preferably, the dose range for Thyex oral administration is from about 1 mg/kg to about 10 mg/kg. Even more preferably, the dose range for Thyex oral administration is from about 3 mg/kg to about 9 mg/kg. Most preferably, the dose range for Thyex oral administration is from about 5 mg/kg to about 8 mg/kg.

In particular aspects, the daily dose range for adjunctive administration of beta glucan can be determined by routine optimization by one of ordinary skill in the art. In particular aspects, the daily dose range for adjunctive administration of the polysaccharide extract (e.g., consisting of about 70% beta 1-3 glucan and 30% tissue proteins) will be about 300 to about 500 mg per day for a typical patient (e.g., or about 0.5 mg/kg to 15 mg/kg). In particular embodiments, using more highly purified polysaccharide fractions (e.g., void of protein; e.g., extracted by the method of Ohno et al (*Biol Pharm Bul,* 23, p 866, 2000), the daily dose will be about 300 mg per day (e.g., or about 0.5 mg/kg to 2.0 mg/kg) for a typical patient.

Preferably, as in the Examples herein, the DYXC-1 and 2 distillate compositions are standardized at a value of about 200 mg (dried herb wt equivalents; dhe)/ml.

Preferably, in terms of dried herb wt equivalents, the daily dose range for DYXC-1 administration injection is from about 5 mg/kg to about 50 mg/kg. More preferably, the dose range for DYXC-1 administration by injection is from about 10 mg (dhe)/kg to about 40 mg (dhe)/kg. Even more preferably, the dose range for DYXC-1 administration by injection is from about 15 mg (dhe)/kg to about 30 mg (dhe)/kg. Most preferably, the dose range for DYXC-1 administration by injection is from about 20 mg (dhe)/kg to about 25 mg (dhe)/kg.

Formulations and Use

In particular preferred aspects, Thyex-1-6A and -6B have substantial utility in methods for treatment of various Human and mammalian conditions including, but not limited to arthritis, mobility deficits, gout, rheumatoid arthritis (RA), osteoarthritis (OA), and pseudogout, and/or inflammation resulting from any of the conditions comprising administration of said compositions.

For administration by injection, the Thyex, and the D-YXC-1 compositions of the present invention are preferably formulated in aqueous solutions with physiologically compatible buffered saline (e.g., phosphate buffered standard physiological saline; 0.85% NaCl).

For oral administration, the pharmaceutical Thyex and DYXC-2 compositions of the present invention may take the form of, for example, liquids, gels, syrups, slurries, and the like, prepared by conventional means with pharmaceutically acceptable excipients such as: binding agents (e.g., pre-gelatinized maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP)); fillers (e.g., lactose, sucrose, mannitol, or sorbitol, microcrystalline cellulose or calcium hydrogen phosphate); lubricants (e.g., magnesium stearate, talc or silica); disintegrants (e.g., potato starch, sodium starch glycolate, cross-linked polyvinyl pyrrolidone, agar, or alginic acid or a salt thereof such as sodium alginate); or wetting agents (e.g., sodium lauryl sulfate). Such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

For administration by inhalation, the Thyex compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

The Thyex, and the D-YXC-1 compositions of the present invention may be formulated for parenteral administration by injection by bolus injection or continuous infusion. Formulations for injection may be presented in unit dosage form in ampoules or in multi-dose containers, with optionally, with an added preservative.

Vaccines are either those commercially available, or those prepared according to art-recognized methods, and are of various forms, including conventional forms such as aqueous dispersions, oil emulsions, liposome compositions, lyophilized forms, etc. Vaccine compositions and vaccination regimens may comprise different adjuvants, emulsifiers, stabilizers, etc. Vaccines are administered by different routes, including but not limited to parenteral, intramuscular, intranasal, intratracheal, subcutaneous, cutaneous, percutaneous or intracutaneous routes, and combinations thereof.

Vaccines may be prepared, inter alia, as aqueous solutions, syrups, elixers, or tinctures, and the liquid formulations may include suspensions and/or emulsions.

Thyex-4 may be lyophilized and dispensed in "00" size gelatin capsules: Oral. Approximately 40% thymic polypeptides. According to particular aspects, Thyex-4 may be used for stimulation of immune functions, to treat allergy and certain autoimmune disorders (e.g. arthritis, including: rheumatoid arthritis (RA) and osteoarthritis (OA)); and for treating gout and pseudogout.

Thyex-5. In particular aspects, Thyex-5 (e.g., lyophilized; approximately 80% thymic polypeptides) is mixed with other extracts (e.g. extracts containing polysaccharides such as beta 1-3 glucan). The mixtures, for example, can be dispensed in "00" gelatin capsules, or alternatively, for example, in size "3" capsule if not mixed with other extracts.

Thyex 6A. In particular aspects, Thyex-6A (e.g., sterile liquid extract) can be used to generate aerosols (e.g. for treating pneumonia or emphysema). Alternatively, for example, ointments can be used when Thyex-6A is mixed with water-soluble ointment base for treating, for example, arthritis and gout.

Thyex 6B. In particular aspects, Thyex-6BA (e.g., sterile liquid buffered, and saline adjusted for injection; at least 99% pure) is used for veterinary and human uses, including, but not limited to veterinary uses including: arthritis, mobility deficits, gout, rheumatoid arthritis (RA), osteoarthritis (OA), and pseudogout, and/or inflammation resulting from any of the conditions, etc., and Human uses including, but not limited to: autoimmune disorders (IV or SQ) such as rheumatoid arthritis, mobility deficits, gout, osteoarthritis (OA), and pseudogout, and/or inflammation resulting from any of the conditions.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

The injection-use formulations can be presented in unit-dose or multi-dose sealed containers, such as ampules and vials, and can be stored in a freeze-dried (lyophilized) condition requiring only the addition of the sterile liquid excipient, or the heat-distilled *Houttuynia cordata* extract (DYXC-1 and 2), immediately prior to use. Extemporaneous injection solutions and suspensions can be prepared from sterile powders, granules, and tablets. The requirements for effective pharmaceutical carriers for injectable compositions are well known to those of ordinary skill in the art. See, for example, Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include lozenges comprising a heat-distilled *Houttuynia cordata* extract (DYXC-1 and 2) of the invention and optionally, an additional therapeutic and a flavor, usually sucrose and acacia or tragacanth; pastilles comprising a gas-enriched fluid and optional additional therapeutic agent in an inert base, such as gelatin and glycerin, or sucrose and acacia; and mouth washes or oral rinses comprising a gas-enriched fluid and optional additional therapeutic agent in a suitable liquid carrier; as well as creams, emulsions, gels, and the like.

Additionally, formulations suitable for rectal administration may be presented as suppositories by mixing with a variety of bases such as emulsifying bases or water-soluble bases. Suitable pharmaceutical carriers are described in Remington's Pharmaceutical Sciences, Mack Publishing Company, a standard reference text in this field.

The dose administered to a subject, especially an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the condition being treated. A suitable dose is that which will result in a concentration of the therapeutic composition in a subject that is known to affect the desired response.

The size of the dose also will be determined by the route, timing and frequency of administration as well as the existence, nature, and extent of any adverse side effects that might accompany the administration of the therapeutic composition and the desired physiological effect.

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

EXAMPLE 1

Preparation of Thymus Extracts Thyex-1

This example provides an exemplary process embodiment used for preparing thymus extracts, and compositions ("Thyex-1") produced in accordance therewith:

Thyex-1:

Thyex-1 process. The following steps (1)-(16) comprise a process embodiment for producing Thyex-1 (step (17) relates to storage) suitable for oral delivery:

(1) Homogenization of thymus tissue. Fresh "prime" (i.e., not fibrous or whitish in appearance) porcine, ovine, or bovine thymus glands were frozen (e.g., overnight). The frozen glands were rinsed briefly in clean water and "dressed" by removal of any associated fibrous or connective tissue, fatty tissue, or lymph node tissue. The prime washed, dressed thymus glands were cut into small pieces (e.g., about 2" cubes using a sharp knife), and homogenized through the use of a food processor or other grinding apparatus (e.g., a meat grinder). For homogenization, a volume of approximately 700 ml of 0.2% NaCl solution (in distilled water) was blended with approximately 350 g wet weight (about 400 ml wet volume) of cut-up thymus tissue in a standard size blender for at least one minute to produce a thymus homogenate;

(2) Low-speed Centrifugation. The "thymus homogenate" of step (1) was centrifuged at about 3,500×G for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Production of a "secondary filtered supernatant." Steps (1)-(3) were repeated with another 350 g wet weight (about 400 ml wet volume) of prime washed, dressed, cut-up thymus glands, except that the "primary filtered supernatant" of step (3) was used in place of the 700 ml of 0.2% NaCl solution of step (1). This substitution allowed for the production of a more concentrated (relative to the "primary filtered supernatant") secondary filtered supernatant;

(5) Heat denaturation. The "secondary filtered supernatant" of step (4) was heated to a temperature of about 75-80° C. by exposing the container thereof to a uniform heat source, such as a constant temperature water bath set at about 100° C., or a double boiler containing water at about 100° C. During said heating, the "secondary filtered supernatant" was frequently agitated or stirred until it reached about 75-80° C. to produce a heat-denatured secondary filtered supernatant;

(6) Low-speed Centrifugation. The "heat-denatured secondary filtered supernatant" of step (5) was centrifuged at 3,500×g for 5 minutes at ambient temperature to produce a pellet and a heat-denatured supernatant fraction;

(7) Production of a "heat-denatured filtered supernatant." The "heat-denatured supernatant fraction" of step (6) was decanted from the centrifugation pellets and gravity filtered through one or more layers of standard cheese cloth to produce a filtered, heat-denatured supernatant fraction (hereinafter the "intermediate supernatant" fraction) that was still slightly warm from the heat denaturation of step (5);

(8) Ammonium sulfate precipitation. About 650 gm of ammonium sulfate was added to 1 L of the warm "intermediate supernatant" of step (7). The solution was stirred until all the ammonium sulfate was dissolved, and then allowed to stand for about 1 hour at ambient temperature to produce a salted intermediate supernatant fraction;

(9) Low-speed centrifugation. The "salted intermediate supernatant" of step (8) was divided between two, 1 L centrifuge bottles and centrifuged at 3,500×g for 10 minutes at ambient temperature to produce ammonium sulfate pellets, and supernatant fractions;

(10) Suspension of ammonium sulfate pellet fraction. The "ammonium sulfate supernatants" from step (9) were decanted from the centrifugation tubes and discarded, and excess salt solution was carefully wiped from the inside tube walls. The two ammonium sulfate pellets of step (9) (i.e., corresponding to each 1-L centrifuge bottle) were then suspended and dissolved by gentle mixing with about 50 ml of 0.01 to 0.05 M phosphate buffer (about pH 7) for each pellet (alternatively, the pellets were suspended with distilled water). The suspensions were allowed to stand for about 1 hour at ambient temperature with brief agitation about every 15 minutes (to facilitate complete dissolution of the pellets) to provide an ammonium sulfate fraction. Note that dissolution of any remaining ammonium sulfate pellet can be affected by the step-wise addition of small amounts of distilled water (e.g., 5 ml aliquots), followed by agitation until the pellet is completely dissolved;

(11) Dialysis. The "ammonium sulfate" fraction of step (10) was transferred to clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C. to produce a dialyzed ammonium sulfate fraction. The distilled water was changed every 12 hours. Increasing hydrostatic pressure within the dialysis tubing was periodically relieved by removing some of the dialysate and transferring it to additional dialysis tubes;

(12) High-speed centrifugation. The "dialyzed ammonium sulfate fraction" of step (11) was centrifuged at 8,500×g for 10 minutes at ambient temperature to produce a pellet and dialyzed ammonium sulfate supernatant fraction;

(13) First exclusion-membrane filtration. The "dialyzed ammonium sulfate supernatant fraction" of step (12) was passed under nitrogen pressure at about 40-50 p.s.i. through a 100 kDa exclusion limit membrane filter (Amicon) at 4° C. (alternatively, ambient temperature will suffice) to produce a 3.5 kDa to 100 kDa filtrate;

(14) Second exclusion-membrane filtration. The "3.5 kDa to 100 kDa filtrate" of step (13) was passed under nitrogen pressure at 40 to 50 p.s.i. (275.8 to 344.75 Kpa, in metric units) through a 30 kDa exclusion limit membrane filter (Amicon) to produce a 3.5 kDa to 30 kDa filtrate;

(15) Adjustment of pH and ionic strength. About 5 ml of 1 M phosphate buffer (about pH 7) per liter was added to the "3.5 kDa to 30 kDa filtrate" of step (14). Solid NaCl was then added to 0.85% (weight to volume) to produce a pH- and ionic strength-adjusted 30 kDa filtrate, Thyex-1;

(16) Filter sterilization. The "Thyex-1" of step (15) was filter sterilized by passage through a 0.2µ membrane filter to produce sterile Thyex-1, suitable for oral delivery or delivery; and

(17) Storage. Thyex-1, produced in accordance with steps (1)-(16) of the Thyex-1 process, was typically stored frozen (e.g., −5° C. to −20° C.) in sterilized containers, and thawed just prior to use. According to particular aspects, the therapeutic activity of Thyex-1 was found to be stable to repeated freezing and thawing. Alternatively, Thyex-1 was lyophilized, stored at ambient temperature and reconstituted with sterile water prior to use.

According to particular aspects, one or more of the above steps are optional.

EXAMPLE 2

Preparation of Thymus Extracts Thyex-2

This example provides an exemplary process embodiment used for preparing thymus extracts, and compositions ("Thyex-2") produced in accordance therewith suitable for oral delivery:

Thyex-2:

Thyex-2 process. The following steps (1)-(8) comprise a process embodiment for producing Thyex-2 (step (9) relates to storage):

(1) Production of "intermediate supernatant." Steps (1)-(7) of the above-identified Thyex-1 process for the preparation of "intermediate supernatant" were followed (except that steps (1)-(3) were not repeated as in the Thyex-1 process) to produce an "intermediate supernatant" fraction;

(2) High-speed centrifugation. The "intermediate supernatant" fraction of step (1) was cleared (i.e., to remove potential pathogens) by centrifugation at 8,500×g for 10 minutes at ambient temperature to produce a pellet and a cleared intermediate supernatant fraction;

(3) Lyophilization. The "cleared intermediate supernatant" fraction of step (2) was lyophilized (i.e., freeze dried) either to complete dryness to produce a dried, cleared intermediate supernatant fraction, or until its volume was reduced by 90% to produce a lyophilized, cleared intermediate supernatant fraction;

(4) Dialysis. The "lyophilized, cleared intermediate supernatant," or the alternative completely "dried" fraction (suspended in 500 ml distilled water per 13.6 kg (30 lbs.) wet weight of thymus glands processed) of step (3) was dialyzed according to step (11) of the above-identified Thyex-1 process to produce a dialyzed, lyophilized intermediate supernatant fraction;

(5) High-speed centrifugation. The "dialyzed, lyophilized intermediate supernatant" of step (4) was centrifuged at 8,500×g for 10 minutes at ambient temperature to produce a pellet, and a cleared, dialyzed, lyophilized intermediate supernatant fraction;

(6) Exclusion-Membrane filtration. The "cleared dialyzed, lyophilized intermediate supernatant" of step (5) was passed consecutively under nitrogen pressure (40-50 p.s.i.) through 100 kDa and 30 kDa exclusion limit membrane filters (Amicon), according to steps (13) and (14) of the above-identified Thyex-1 process to produce a 3.5 kDa to 30 kDa filtrate. The protein concentration of the "30 kDa filtrate" was measured, and optionally diluted (typically, to about 2 mg/0.25 ml (lesser or greater dilutions were also made as desired);

(7) Adjustment of pH and ionic strength. The pH and ionic strength of the "3.5 kDa to 30 kDa filtrate" or the optionally diluted "3.5 kDa to 30 kDa filtrate" of step (6) was adjusted according to step (15) of the above-identified Thyex-1 process to produce a pH- and ionic strength-adjusted 3.5 kDa to 30 kDa filtrate, Thyex-2;

(8) Filter sterilization. The "Thyex-2" of step (7) was filter sterilized according to step (16) of the above-identified Thyex-1 process to produce sterile Thyex-2, suitable for oral delivery; and (9) Storage. Thyex-2, produced in accordance with steps (1)-(8) of the Thyex-2 process was typically stored frozen (e.g., −5° C. to −20° C.) in sterilized containers, and thawed just prior to use. According to particular aspects, the therapeutic activity of Thyex-2 was found to be stable to repeated freezing and thawing. Alternatively, Thyex-2 was lyophilized, stored at ambient temperature and reconstituted with sterile water prior to use.

According to particular aspects, one or more of the above steps are optional.

EXAMPLE 3

Preparation of Thymus Extracts Thyex-3

This example provides an exemplary process embodiment used for preparing thymus extracts, and compositions ("Thyex-3") produced in accordance therewith suitable for oral delivery:

Thyex-3:

Thyex-3 process. The following steps (1)-(10) comprise a process embodiment for producing Thyex-3 (step (11) relates to storage), suitable for oral delivery:

(1) Homogenization of thymus tissue. Fresh "prime" (i.e., not fibrous or whitish in appearance) porcine or bovine thymus glands were frozen (e.g., overnight). The frozen glands were rinsed briefly in clean water and "dressed" by removal of any associated fibrous or connective tissue, fatty tissue, or lymph node tissue. The prime washed, dressed thymus glands were cut into small pieces (e.g., about 2" cubes using a sharp knife), and homogenized through the use of a food processor or other grinding apparatus (e.g., a meat grinder). For homogenization, a volume of approximately 800 ml of 0.2% NaCl solution (in distilled water) was blended with approximately 300 g wet weight (about 340 ml wet tissue volume) of cut-up thymus tissue in a standard size blender for at least one minute to produce a thymus homogenate;

(2) Low-speed Centrifugation. The "thymus homogenate" of step (1) was centrifuged at about 3,500 rpm for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Production of a "secondary filtered supernatant." Steps (1)-(3) were repeated with another 175 g wet weight (200 ml wet tissue volume) of prime washed, dressed, cut-up thymus glands, except that the "primary filtered supernatant" of step (3) was used in place of the 800 ml of 0.2% NaCl solution of step (1). This substitution allowed for the production of a more concentrated (relative to the "primary filtered supernatant") secondary filtered supernatant;

(5) Production of a "tertiary filtered supernatant." Steps (1)-(3) were repeated with another 200 ml (wet volume) of prime washed, dressed, cut-up thymus glands, except that the "secondary filtered supernatant" from step (4) was used in place of the 800 ml of 0.2% NaCl solution of step (1). This substitution allowed for the production of a more concentrated (relative to the "primary" and "secondary filtered supernatants") tertiary filtered supernatant;

(6) Heat denaturation. The "tertiary filtered supernatant" from step (5) was heated to a temperature of about 75-80° C. by exposing the container thereof to a uniform heat source such as a constant-temperature water bath set at about 100° C. or a double boiler containing water at about 100° C. During heating, the "tertiary filtered supernatant" was frequently agitated or stirred until it reached about 75-80° C. to produce a heat-denatured tertiary filtered supernatant fraction;

(7) Low-speed Centrifugation. The "heat-denatured tertiary filtered supernatant" fraction of step (6) was centrifuged at 3,500 rpm for 5 minutes at ambient temperature to produce a pellet and a heat-denatured supernatant fraction;

(8) Production of a "heat-denatured filtered supernatant." The "heat-denatured supernatant fraction" of step (7) was decanted from the centrifugation pellets and gravity filtered through one or more layers of standard cheese cloth to produce a filtered, heat-denatured supernatant fraction that was still slightly warm from the heat denaturation of step (6);

(9) High-speed centrifugation. The "filtered, heat-denatured supernatant" fraction of step (8) was centrifuged at about 8,500×g for 5 minutes at ambient temperature to produce a pellet, and a high-speed supernatant fraction, Thyex-3;

(10) Filter sterilization. The "Thyex-3" fraction of step (9) was filter sterilized according to step (16) of the above-identified Thyex-1 process to produce sterile Thyex-3, suitable for oral delivery; and

(11) Storage. Thyex-3, produced in accordance with steps (1)-(10) of the Thyex-3 process was typically stored frozen (e.g., −5 to −20° C.) in sterilized containers, and thawed just prior to use. According to particular aspects, the therapeutic activity of Thyex-3 was found to be stable to repeated freezing and thawing. Alternatively, Thyex-3 was lyophilized, stored at ambient temperature and reconstituted with sterile water prior to use.

According to particular aspects, one or more of the above steps are optional.

EXAMPLE 4

Preparation of Thymus Extracts Thyex-4

With reference to FIG. 4, this example provides an exemplary process embodiment used for preparing thymus extracts, and compositions ("Thyex-4") produced in accordance therewith suitable for oral delivery:

Thyex-4:

Thyex-4 process. The following steps (1)-(11) comprise a process embodiment for producing Thyex-4 (step (12) relates to storage), e.g., suitable for oral delivery (NOTE: the following steps (1)-(6) are referred to herein as "stage 1 steps (1)-(6)":

Stage 1 Steps (1)-(6):

(1) Homogenization of thymus tissue. Fresh "prime" (e.g., preferably not fibrous or whitish in appearance) porcine ovine or bovine thymus glands were frozen (e.g., overnight, or in some instances, preferably for at least 72 hours). The frozen glands were rinsed briefly in clean water and "dressed" by removal of any associated fibrous or connective tissue, fatty tissue, or lymph node tissue. The prime washed, dressed thymus glands were cut or minced into small pieces (e.g., about 1" to about 2" cubes using a sharp knife), and homogenized through the use of a food processor or other grinding apparatus (e.g., a meat grinder). For homogenization, a volume of approximately 700 ml of 0.2% NaCl solution (in distilled water) was blended for at least a minute with approximately 350 g wet weight of cut-up thymus tissue in a standard size blender to produce a thymus homogenate;

(2) Low-speed Centrifugation. The "thymus homogenate" of step (1) was centrifuged at about 3,500 rpm for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Heat denaturation. The "primary filtered supernatant" of step (3) was heated to a temperature of about 75-80° C. by exposing the container thereof to a uniform heat source, such as a constant temperature water bath set at about 100° C., or a double boiler containing water at about 100° C. During said heating, the "primary filtered supernatant" was frequently agitated or stirred until it reached about 75-80° C. to produce a heat-denatured primary filtered supernatant;

(5) Low-speed Centrifugation. The "heat-denatured primary filtered supernatant" of step (4) was centrifuged at 3,500×g for 5 minutes at ambient temperature to produce a pellet and a heat-denatured supernatant fraction;

(6) Production of a "heat-denatured filtered supernatant." The "heat-denatured supernatant fraction" of step (5) was decanted from the centrifugation pellets and gravity filtered through one or more layers of standard cheese cloth to produce a filtered, heat-denatured supernatant fraction (hereinafter the "intermediate supernatant" fraction) that was still slightly warm from the heat denaturation of step (4);

Stage 2 Steps (7)-(6):

(7) Dialysis. The "intermediate supernatant" fraction of step (6) was dialyzed according to step (11) of the above-identified Thyex-1 process (e.g., using clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C.) to produce a dialyzed, intermediate supernatant fraction;

(8) Low-speed Centrifugation. The "dialyzed, intermediate supernatant fraction" of step (7) was centrifuged at 3,500 rpm for 5 minutes at ambient temperature to produce a pellet and a heat-denatured supernatant fraction;

(9) Production of a "heat-denatured filtered supernatant." The "heat-denatured supernatant fraction" of step (8) was decanted from the centrifugation pellets and gravity filtered through one or more layers of standard cheese cloth to produce a filtered, heat-denatured supernatant fraction;

(10) High-speed centrifugation. The "filtered, heat-denatured supernatant" fraction of step (9) was centrifuged at about 8,500×g for 5 minutes at ambient temperature to produce a pellet, and a high-speed supernatant fraction, Thyex-4;

(11) Filter sterilization. The "Thyex-4" fraction of step (10) was filter sterilized according to step (16) of the above-identified Thyex-1 process to produce sterile Thyex-4, suitable for oral delivery; and

(12) Storage. Thyex-4, produced in accordance with steps (1)-(11) of the Thyex-4 process was typically stored frozen (e.g., −5 to −20° C.) in sterilized containers, and thawed just prior to use. According to particular aspects, the therapeutic activity of Thyex-4 is stable to repeated freezing and thawing. Alternatively, Thyex-4 was lyophilized, stored at ambient temperature and reconstituted with sterile water prior to use.

According to particular aspects, one or more of the above steps are optional.

EXAMPLE 5

Preparation of Thymus Extracts Thyex-5

With reference to FIG. 4, this example provides an exemplary process embodiment used for preparing thymus extracts, and compositions ("Thyex-5") produced in accordance therewith suitable for oral delivery:

Thyex-5:

Thyex-5 process. The following steps (1)-(13) comprise a process embodiment for producing Thyex-5 (step (14) relates to storage), suitable for oral delivery:

(1)-(6) (see Stage 1 steps (1)-(6) for Thyex-4 above);

(7) Ammonium sulfate precipitation. About 750 to about 800 gm of ammonium sulfate was added to 1 L of the warm "intermediate supernatant" of step (6). The solution was stirred until all the ammonium sulfate was dissolved, and then allowed to stand for about 1 hour at ambient temperature to produce a salted intermediate supernatant fraction;

(8) Low-speed centrifugation. The "salted intermediate supernatant" of step (7) was divided between two, 1 L centrifuge bottles and centrifuged at 3,500×g for 10 minutes at ambient temperature to produce ammonium sulfate pellets, and supernatant fractions;

(9) Suspension of ammonium sulfate pellet fraction. The "ammonium sulfate supernatants" from step (8) were decanted from the centrifugation tubes and discarded, and excess salt solution was carefully wiped from the inside tube walls. The two ammonium sulfate pellets of step (8) (i.e., corresponding to each 1-L centrifuge bottle) were then suspended and dissolved by gentle mixing with about 50 ml of distilled water (or optionally with 0.01 to 0.05 M phosphate buffer (about pH 7)) for each pellet. The suspensions were allowed to stand for about 1 hour at ambient temperature with brief agitation about every 15 minutes (to facilitate complete dissolution of the pellets) to provide an ammonium sulfate fraction. Note that dissolution, if desired, of any remaining ammonium sulfate pellet can be affected by the step-wise addition of small amounts of distilled water (e.g., 5 ml aliquots), followed by agitation until the pellet is completely dissolved;

(10) Dialysis. The "ammonium sulfate" fraction of step (9) was transferred to clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C. to produce a dialyzed ammonium sulfate fraction. The distilled water was changed every 12 hours. Increasing hydrostatic pressure within the dialysis tubing was periodically relieved by removing some of the dialysate and transferring it to additional dialysis tubes;

(11) High-speed centrifugation. The "dialyzed ammonium sulfate fraction" of step (10) was centrifuged at 8,500×g for 10 minutes at ambient temperature to produce a pellet and dialyzed ammonium sulfate supernatant fraction (Thyex-5);

(12) Adjustment of pH and ionic strength. Optionally, about 5 ml of 1 M phosphate buffer (about pH 7) per liter is added to the "dialyzed ammonium sulfate supernatant fraction of step (11). Optionally, solid NaCl is then added to 0.85% (weight to volume) to produce a pH- and ionic strength-adjusted dialyzed ammonium sulfate supernatant fraction (Thyex-5);

(13) Filter sterilization. The "Thyex-5" of step (12) was filter sterilized by passage through a 0.2μ membrane filter to produce sterile Thyex-5, suitable for oral delivery; and

(14) Storage. Thyex-5, produced in accordance with steps (1)-(13) of the Thyex-5 process, was typically stored frozen (e.g., −5° C. to −20° C.) in sterilized containers, and thawed just prior to use. According to particular aspects, the therapeutic activity of Thyex-5 was found to be stable to repeated freezing and thawing. Alternatively, Thyex-5 was lyophilized, stored at ambient temperature and reconstituted with sterile water prior to use.

According to particular aspects, one or more of the above steps are optional.

Above steps (7)-(11) are referred to herein as Stage 2 steps (7)-(11).

EXAMPLE 6

Preparation of Thymus Extracts Thyex-6A

Thyex-6A. With reference to FIG. 4, this example provides an exemplary process embodiment used for preparing thymus extracts, and compositions ("Thyex-6A") produced in accordance therewith suitable for oral delivery, or delivery as a topical ointment or by injection or inhalation:
Thyex-6A:

Thyex-6A process. The following steps (1)-(14) comprise a process embodiment for producing Thyex-6A (step (15) relates to storage), suitable for oral delivery:

(1)-(6) (see Stage 1 steps (1)-(6) for Thyex-4 and Thyex-5 above);

(7)-(11) (see Stage 2 steps (7)-(11) for Thyex-5 above);

(12) First exclusion-membrane filtration. The "dialyzed ammonium sulfate supernatant fraction" of step (11) was passed under nitrogen pressure at about 40-50 p.s.i. through a 100 kDa exclusion limit membrane filter (Amicon) at 4° C. (alternatively, ambient temperature will suffice) to produce a 3.5 kDa to 100 kDa filtrate;

(13) Second exclusion-membrane filtration. The "3.5 kDa to 100 kDa filtrate" of step (12) was passed under nitrogen pressure at 40 to 50 p.s.i. (275.8 to 344.75 Kpa, in metric units) through a 30 kDa exclusion limit membrane filter (Amicon) to produce a 3.5 kDa to 30 kDa filtrate (Thyex-6A);

(14) Filter sterilization. The "Thyex-6A" of step (13) was filter sterilized by passage through a 0.2μ membrane filter to produce sterile Thyex-6A, suitable for oral delivery, or delivery as a topical ointment or by injection or inhalation; and

(15) Storage. Thyex-6A, produced in accordance with steps (1)-(14) of the Thyex-6A process, was typically stored frozen (e.g., −5° C. to −20° C.) in sterilized containers, and thawed just prior to use. According to particular aspects, the therapeutic activity of Thyex-6A was found to be stable to repeated freezing and thawing. Alternatively, Thyex-6A was lyophilized, stored at ambient temperature and reconstituted with sterile water prior to use.

According to particular aspects, one or more of the above steps are optional.

EXAMPLE 7

Preparation of Thymus Extracts Thyex-6B

Thyex-6B process. With reference to FIG. 4, this example provides an exemplary process embodiment used for preparing thymus extracts, and compositions ("Thyex-6B") produced in accordance therewith suitable for oral delivery, or delivery as a topical ointment or by injection or inhalation:
Thyex-6B:

Thyex-6B process. The following steps (1)-(15) comprise a process embodiment for producing Thyex-6A (step (16) relates to storage), suitable for oral delivery, or delivery as a topical ointment or by injection or inhalation:

(1)-(6) (see Stage 1 steps (1)-(6) for Thyex-4, -5 and -6A above);

(7)-(11) (see Stage 2 steps (7)-(11) for Thyex-5 and -6A above);

(12) First exclusion-membrane filtration. The "dialyzed ammonium sulfate supernatant fraction" of step (11) was passed under nitrogen pressure at about 40-50 p.s.i. through a 100 kDa exclusion limit membrane filter (Amicon) at 4° C. (alternatively, ambient temperature will suffice) to produce a 3.5 kDa to 100 kDa filtrate;

(13) Second exclusion-membrane filtration. The "3.5 kDa to 100 kDa filtrate" of step (12) was passed under nitrogen pressure at 40 to 50 p.s.i. (275.8 to 344.75 Kpa, in metric units) through a 30 kDa exclusion limit membrane filter (Amicon) to produce a 3.5 kDa to 30 kDa filtrate (Thyex-6B);

(14) Adjustment of pH and ionic strength. Optionally, about 5 ml of 1 M phosphate buffer (about pH 7) per liter is added to the "dialyzed ammonium sulfate supernatant fraction of step (13). Optionally, solid NaCl is then added to 0.85% (weight to volume) to produce a pH- and ionic strength-adjusted dialyzed ammonium sulfate supernatant fraction (Thyex-6B);

(15) Filter sterilization. The "Thyex-6B" of step (14) was filter sterilized by passage through a 0.2μ membrane filter to produce sterile Thyex-6B, suitable for oral delivery, or delivery as a topical ointment or by injection or inhalation; and

(16) Storage. Thyex-6B, produced in accordance with steps (1)-(15) of the Thyex-6B process, was typically stored frozen (e.g., −5° C. to −20° C.) in sterilized containers, and thawed just prior to use. According to particular aspects, the therapeutic activity of Thyex-6B was found to be stable to repeated freezing and thawing. Alternatively, Thyex-6B was lyophilized, stored at ambient temperature and reconstituted with sterile water prior to use.

According to particular aspects, one or more of the above steps are optional.

EXAMPLE 8

General Considerations for Practice of the Above-Identified Thyex 1-6A and -6B Process Embodiments This Example 8 provides general considerations for practice of the above-identified Thyex 1-6A and -6B process embodiments.

The above-described embodiments (Thyex-1 (steps 1-16), Thyex-2 (steps 1-8), Thyex-3 (steps 1-10), Thyex-4 (steps 1-11), Thyex-5 (steps 1-13), Thyex-6A (steps 1-14) and Thyex 6B (steps 1-15)), and the storage (e.g., lyophilization) steps of the inventive processes may be practiced with various modifications (including but not limited to those outlined below) that are within the scope of the present invention, and with alternatives or substitutions that will be recognized by those of ordinary skill in the art as being equivalent to those used herein to produce Thyex 1-6A and -6B.

Thymus glands. In particular aspects, animals (e.g., steers) are taken to a packing house at about 12-14 months. The thymus gland at this age is grayish. As an animal ages, the gland begins to become fibrous and even whitish in color. The optimum yield of final product from one kilogram (about 4.5 lb) of prime gland is 1 gram of purified Thyex (e.g., Thyex 6A or 6B). Sheep and pig glands are generally from 6 month-old animals.

Freshly harvested thymus glands from porcine, ovine, or bovine sources should optimally be frozen within 24 hours of harvest and stored frozen, preferably for at least 72 hours. Freezing of the thymus glands renders the cells more susceptible to disruption in isotonic salt solution (e.g., 0.2% to 0.3% salt, such as NaCl) during homogenization. Variations in the freezing temperature and duration are within the scope of the present invention. The thymus glands are preferably frozen at least once (e.g., −5 to −20° C.) for production of optimal extracts.

For example, to process, thawed glands are preferably first washed and extraneous materials, such as fatty tissues, lymph nodes, and connective tissues are preferably excised and discarded. The tissues are preferably minced into approximately 1" squares before subjected to grinding (e.g., in a food processor, meat grinder, blender, or equivalent or suitable device). Preferably, the ground glands are homogenized in a blender at a proportion of about 350 gm wet weight with 700 ml of 0.2% saline for at least a minute. Following centrifugation (e.g., about 3,500×g for 10 minutes), the supernatant solution (upper and lower ppt discarded) is heat denatured by raising the solution temperature in a double boiler with constant stirring to a temperature in the range of about 75° C. to 80° C. (preferably 75° C.). Following a second centrifugation at, e.g., the same speed but for 5 minutes, the supernatant solution is collected and precipitate (ppt) discarded. In particular embodiments, the glands for all Thyex processes 1, 2, 3, 4, 5, 6A, and 6B are processed through this phase in identical or very similar fashion.

Production of "secondary"- and "tertiary"-filtered supernatants, such as those described in step (4) of the Thyex-1 process embodiment, step (1) of the Thyex-2 process embodiment, or steps (4) and (5) of the Thyex-3 process embodiment, allows for more concentrated filtered supernatants (relative to the corresponding "primary"-filtered supernatants), thus reducing the amount of ammonium sulfate required (Thyex-1 process embodiment), or the lyophilization time required (Thyex-2 process embodiment) to process a given amount of thymus tissue. Generally, variations in the final protein concentrations (e.g., in the range of 1 to 7 mg/ml) of the various primary-, secondary- and tertiary-filtered supernatants reflect the average age of the animals from which thymus tissue is obtained. Preferably, the protein concentration of the tertiary-filtered supernatant is about 4 mg/ml.

A heat-denaturation step is integral to all of the above-described Thyex process embodiments, and facilitates precipitation and subsequent removal of relatively large, heat-labile proteins that have no utility in the claimed compositions or methods (see below). Variation in the volume of filtered supernatant fraction treated, in the final temperature of the heat-denaturation step (within the range of about 72° C. to about 75° C.), in the temperature of the uniform heat source (within the range of about 80° C. to about 100° C., preferably about 100° C.) and in the time period over which heating of the filtered supernatant fractions from initial to said final temperature takes place (generally within the range of about 5 to 20 minutes for a 1-liter volume of supernatant, but generally for lesser or greater periods of time when heating smaller or larger volumes, respectively) are within the scope of the present invention. Preferably, the supernatant is heated to the final temperature at a rate that is as rapid as possible whereby said rate, in combination with stirring, generally minimizes the occurrence of local supernatant temperatures (e.g., supernatant temperatures near the heat-transferring wall of the supernatant container) that exceed the desired final temperature.

Likewise, variations in the duration and frequency of stirring during said heating are within the scope of the present invention, and depend on the temperature of the constant-temperature heat source and the volume of supernatant being heated. Generally, both the duration and frequency of stirring increase with increasing supernatant volume or heat-source temperature. Constant stirring is also effective, and preferable when heating relatively large supernatant volumes.

Step (8) of the above-described Thyex-1 process embodiment, and step (7) of the above-described Thyex-5, -6A and -6B process embodiment involves protein concentration/fractionation by ammonium sulfate precipitation of the "intermediate supernatant" fraction. Most preferably, solid ammonium sulfate is added to attain high salt concentrations (e.g., in excess of about 0.7 gm/ml) with minimal dilution. Alternatively, this concentration/fractionation step is achieved by adding saturated ammonium sulfate solution. However, because dilution of the intermediate supernatant fraction is preferably minimized, this embodiment results in relatively lower final salt concentrations (e.g. of about 0.5 gm/ml or greater), and is thus less efficient in precipitating (and thereby recovering) desirable low molecular weight proteins. Nonetheless, according to particular aspects, the resulting Thyex compositions have activity in the claimed methods, albeit to a lesser degree. Moreover, the present invention also encompasses the use of combinations of saturated or sub-saturated ammonium sulfate solutions with solid ammonium sulfate.

A dialysis steps of the above-described Thyex process embodiments, allow any molecules of molecular weight less that about 3.5 kDa to pass through. Variation in the precise exclusion limit of the dialysis membrane is within the scope of the present invention. Generally, any dialysis membrane is acceptable provided that its exclusion limit (porosity) enables the retention of molecules having molecular weights of about 5 kDa or larger.

Additionally, variation in the precise exclusion limits of the filtration membranes used in membrane filtrations steps of the Thyex process embodiments are within the scope of the present invention. Generally, any such filtration membrane is acceptable provided that its exclusion limit (porosity) does not result in exclusion (i.e., removal from the final Thyex composition) of molecules having molecular weights equal to or smaller than about 15 kDa. For example, exclusion membranes that exclude molecules of about 20, 30 or 40 kDa or larger are useful in the practice of the present invention, but result in final Thyex compositions that are less active per mg of final protein, compared to those compositions prepared using an exclusion membrane the excludes proteins larger than about 15 kDa. Preferably, dialysis and filtration membranes are chosen such that the resulting Thyex compositions comprise proteins in the molecular weight range of about 5 to 14 kDa.

The process embodiments (e.g., Thyex-3) may further comprise fractionation, based on molecular weight, to obtain a final protein fraction having proteins of about 3.5 to about 30 kDa.

Many different types of membrane filters (e.g., cellulose acetate membranes; Millipore), are commercially available for use in filter sterilization procedures. Some commercially-available membrane filters are self contained and provided as pre-sterilized, disposable units. Other membranes are mounted in reusable membrane holders, and heat sterilized in an autoclave prior to use.

Preferably, the final Thyex 1-6A and -6B compositions are standardized at a protein concentration about 1 mg/ml, based on optical density at 260 and 280 nm. Preferred dosages are discussed herein above under "Dose Determinations."

The instant processes comprise steps to optimize protein compositions for therapeutic use. For example, the above-described Thyex 6A and Thyex 6B process embodiments are designed to provide therapeutic compositions suitable for delivery as a topical ointment or by injection or inhalation, and include ammonium sulfate precipitation/fractionation steps. Thyex-5 is prepared from a similar process but is somewhat less refined than Thyex-6A or Thyex-6B, and is designed to be preferably mixed in appropriate ratios with extracted lyophilized herbal sources and administered orally in, for example, filled gelatin capsules. The Thyex-4 process embodiment lacks ammonium sulfate precipitation step but provides for a sufficiently-concentrated composition after lyophilization. The resulting Thyex-4 composition is less refined in relative to those of Thyex-5 (and Thyex-6A and -6B) but is nonetheless suitably concentrated and formulated for efficacious oral delivery in both animals and humans.

EXAMPLE 9

Treatment of Gouty Arthritis Using the Inventive Thyex Compositions and Combinations Thereof Overview. Gout is a very painful and debilitating disorder that has both diet and genetic components. The disease is characterized by high levels of uric acid circulating in the blood, eventually this results in urate crystals settling in tissues of the joints. In certain embodiments this build up of urate crystals in joints causes immune cells to infiltrate the surrounding tissue and cause inflammation. According to particular embodiments, the inventive Thyex compositions have substantial utility for affecting aspects of the immune system and have utility for limiting the inflammatory response, or have substantial utility for limiting the build-up of urate crystals.

Gouty Arthritis:

In one instance involving Weak Calf Syndrome, afflicted newborn calves were too weak to rise/nurse and had a mortality rate of over 95%. Calves afflicted with the disease were treated every other day with thyex (e.g., Thyex-1-6A and -6B) via injection. Approximately 72 hours after a first thyex injection the symptoms (e.g., the initial arthritic condition) of the majority of the treated animals appeared abated. In addition, most of the treated animals grew to normal size, instead of the stunted growth normally seen in the afflicted animals. However, a small portion of the treated animals did not grow normally and only grew to one-half the size of their normal counterparts. These "runts", although showing initial improvement after the first few injections, began showing gradual signs of lethargy. When tested these animals were found to be chronically ill as evidence by their prolonged parasitemia (e.g., *Hemobartonella* and a *Trypanosoma* sp.). A subset of these runts were treated every other day with thyex (e.g., Thyex-1-6A and -6B) via injection. Parasites began disappearing from the blood and all treated animals showed evidence of renewed growth when compared to untreated controls within a few days of treatment. According to certain embodiments, the thyex treatment resulted in release of growth hormones from the pituitary, which enabled renewed growth. According to further embodiments, the thyex treatment stimulated the immune system, which enabled the treated animals to recover from the chronic infections.

According to certain embodiments, the calves were unable to rise and nurse due primarily to the acute polyarthritic condition of their hocks. According to particular embodiments relating to gouty arthritis, therefore, administration of Thyex modulates at least one of inflammatory response and urate crystal build-up.

In further limited trials, regular scheduled injections with Thyex for the afflicted calves resulted in new growth of the survivors. According to certain embodiments and without being bound by theory, the affect of Thyex on calves is explained by limiting infiltration of immune cells into gouty joints. This in turn limited the painful swelling associated with gout and allowed the calves to behave normally, for example greater mobility and ability to rise and nurse.

EXAMPLE 10

Treatment of Arthritic Animals with the Inventive Thyex Compositions and Combinations Thereof Several old arthritic dogs, whose symptoms included difficulty walking and irritability to petting and touching, were treated with Thyex at regular schedules. The treated dogs showed partial or complete relief from arthritic pain, and resumed daily jogging and normal activities and they did so without any signs of pain.

According to additional aspects of the present invention, and without being bound by mechanism, these observations are explained, at least in part, by modulation of the immune system. According to particular aspects, Thyex limits the inflammation process and thereby reduces the destruction of joints in arthritic dogs.

EXAMPLE 11

Treatment of Gouty Arthritis with the Inventive Thyex Compositions in Combination with at Least One Other Agent According to particular aspects of the present invention, the inventive Thyex compositions are optionally administered with a polysaccharide extract (e.g., to stimulate macrophage) to treat gouty arthritis (e.g., by modulating T cells). In certain aspects, administration of Thyex alone is sufficient, but results are improved by administration of polysaccharide.

Beta glucans. Various investigators, including the present Applicant, have reported that administering BCG showed limited success for treatment. Due to various problems in using BCG, however, the Applicant has sought other alternative means to activate macrophage and to complement the inventive Thyex compositions.

According to particular aspects, polysaccharides, such as beta glucan consisting of complex sugars found in cell walls of yeasts and mushrooms, are a preferred agent in combination with the inventive Thyex compositions, and act synergistically in combating arthritis and other related conditions.

There are three forms of beta glucan based on the linkages of the complex sugars, and these are recognized as beta-1, 3 or 1,4, and 1,6 glucan. Most are in the form of 1,3 and 1,4, or 1,3 and 1,6, but the 1,3 form, which is most abundant in the fruiting bodies of certain mushrooms (e.g., *Sparassis crupa* or Cauliflower mushroom; or *Lentinula edodes* or shitake, etc.).

A reference by Ohno, Miura, Nakajima, and Yadomae (2000, Biol. Phar. Bull. 23, 866-872) describes a procedure for extracting beta glucan from shitake mushroom. Recently, two firms in Japan have successfully cultured the cauliflower mushroom (aka Hanabaritake), and the Applicant has obtained cauliflower mushroom powder form from these firms.

According to particular aspects, a preferred polysaccharide comprises one or more of the beta glucans, including three types based on the linkages: 1-3, 1-4, and 1-6). A number of commercial beta glucan products are available with most being derived from the common yeast. According to particular aspects, however, the preferred sources are mushrooms; with shitake being most common because of its ready availability/source, and cauliflower mushroom (*Sparassis crupa*), which is preferred as it contains beta 1-3 glucans, but unfortunately has limited availability. Additionally, the shitake mushroom, which is most widely available, is reported to contain the 1-3 glucan and chitin.

According to particular aspects, an oral route of administration is favorable, possibly because the intestinal walls are sites containing large amounts of lymph nodes and thus T cells.

Additional Combination Agents and/or Therapies:

As indicated above, preferred aspects comprise treatment of aging using Thyex compositions in combination with other fungal and/or herbal preparations, including the following:

*Paresis crepe* (aka cauliflower mushroom or hanabaritake) preparations, comprising beta 1-3 glucan, can be used to stimulate macrophage in combination with the inventive Thyex compositions.

*Lentinula edodes* (shitake; e.g., alkaline digest according to the procedure reported by Ohno et al. (Biol. Phar. Bull. 23 866-872, 2000), comprises beta 1-3 glucan and chitin, and can be used for treating arthritis-related illness in combination with the inventive Thyex compositions.

*Astralagas membranaceus* (*Scutellaria baicalensis, Houttuynia cordata*; hot water extract of ground herbs and secondary extraction by alkaline digest as above), stimulate macrophages, and can be used for treating arthritis related illness in combination with the inventive Thyex compositions.

*Lilium longiforum* (aka Easter lily; to prepare extract, leaves are pre-frozen, blended (homogenized) in water, and boiled. The liquid extract centrifuged and the supernatant solution distilled (approximately one-half volume is collected)), can be used for treating arthritis-related illness in combination with the inventive Thyex compositions.

*Houttuynia cordata* (as mentioned above) extracts from leaves (e.g., processed as described herein in Example 10) can be used for treating arthritis-related illness in combination with the inventive Thyex compositions. According to particular aspects, DYXC has substantial utility to treat nausea in both humans and animals caused by illnesses, infections, or other treatments, and in particular embodiments is used in combination with one or more of the inventive Thyex compositions, plus or minus standard additional drugs.

EXAMPLE 12

Treatment of Gouty Arthritis with the Inventive Thyex Compositions

By Injection

According to particular aspects, a human subject is treated for symptoms related to gout by injecting him subcutaneously under a regimen of 1 cc (e.g., per day) of the inventive Thyex composition. One treatment is sufficient to provide for relief from gouty arthritis, and this relief is quickly apparent (e.g., within one to three days). In certain embodiments and without being bound by mechanism, the inventive Thyex compositions modulate the immune system, and reduce inflammation. According to certain embodiments, the pain and swelling symptoms of gouty arthritis are reduced and alleviated due to limiting the inflammatory response.

By Oral Route

Two human subjects were treated for symptoms related to gouty arthritis by oral administration of the inventive Thyex composition (e.g., Thyex-1-6A and -6B; preferably Thyex-6A). Each individual was given 5 capsules, and each consumed 1 capsule daily for 5 days. In the treatment regimen, each patient took one capsule orally of the inventive Thyex composition daily for 5 days. According to particular embodiments and without being bound by theory, the inventive Thyex composition reduced inflammation by modulating the immune system. According to certain embodiments, the pain and swelling symptoms of gouty arthritis are reduced and alleviated due to limiting the inflammatory response.

EXAMPLE 13

Treatment of Osteoarthritis with the Inventive Thyex Compositions

In further aspects, the inventive Thyex compositions (e.g., Thyex-1-6A and -6B) are used to treat individuals with osteoarthritis. Patients are treated orally, by injection, or according to other procedures disclosed herein, with the inventive Thyex compositions to alleviate pain and swelling associated with osteoarthritis. In addition, in certain aspects, treating with the inventive Thyex compositions reduces joint injury associated with osteoarthritis.

Without being bound by theory, the mechanism may comprise modulation of the immune system, which limits inflammation.

EXAMPLE 14

Treatment of Rheumatoid Arthritis with the Inventive Thyex Compositions

In further aspects, the inventive Thyex compositions (e.g., Thyex-1-6A and -6B) are used to treat individuals with rheumatoid arthritis. Patients are treated orally, by injection, or according to other procedures disclosed herein, with the inventive Thyex compositions to alleviate pain and swelling associated with rheumatoid arthritis. In addition, in certain aspects, treating with the inventive Thyex compositions reduces joint injury associated with rheumatoid arthritis.

According to particular aspect and without being bound by theory, the mechanism can comprise stimulation of suppressor T cells, which direct B cells producing the allergy antibodies to stop continued activity and control of reactive T cells. In addition, the mechanism can comprise modulation of the immune system, thereby limiting inflammation. The mechanism can comprise modulation of the immune system, whereby production of the auto-reactive antibodies is lessened.

EXAMPLE 15

Treatment of Pseudogout with the Inventive Thyex Compositions

In further aspects, the inventive Thyex compositions (e.g., Thyex-1-6A and -6B) are used to treat individuals with pseudogout. Patients are treated orally, by injection, or according to other procedures disclosed herein, with the inventive Thyex compositions to alleviate pain and swelling associated with pseudogout. In addition, in certain aspects, treating with the inventive Thyex compositions reduces joint injury associated with pseudogout.

Without being bound by theory, the mechanism can comprise modulation of the immune system, which limits inflammation.

EXAMPLE 16

*Houttuynia cordata* Extracts

Figure 5:
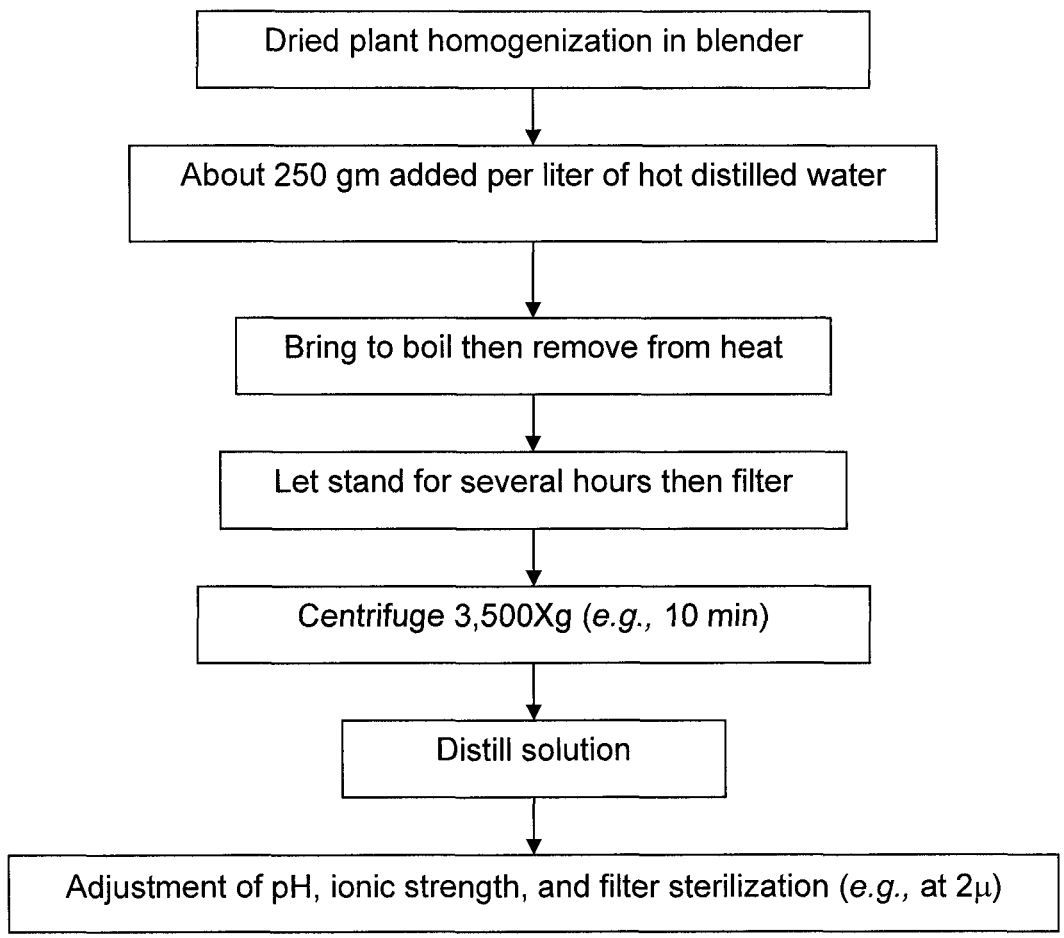
FIG. 5 is a flow diagrammatic representation comprising an inventive D-YXC process embodiment for preparing a *Houttuynia cordata* extract composition.

With reference to FIG. 5, this example provides two process embodiments used to prepare *Houttuynia cordata* extracts, and compositions ("D-YXC-1, and 2") produced in accordance therewith.

*Houttuynia cordata* Thunb, of the family Saururaceae, is a widely known herb (Houttuyniae) from ancient times, and its medicinal effects (particularly of the essential oils of the aerial parts thereof) have been described in various publications relating to herbal medicines (see, e.g., Huang, The Pharmacology of Chinese Herbs, CRC Press, 1999). The steam distillate prepared from fresh plants of *Houttuynia cordata* Thunb has been reported to have in vitro inhibitory activity against some, but not all, enveloped viruses (Hayashi et al., *Planta Med.* 61:237-241, 1995). The herb has also been reported to exhibit antibacterial activity (Huang, supra; Hu, *Zentralbl. Veterinarmed.* 44:365-70, 1997). The herb has been used as a tea for many years, but, as recognized in the art, the process of making the tea (e.g., grinding and boiling the *Houttuynia cordata*) produces a very bitter and unpleasant taste. There are many art recognized methods that attempt to reduce the bitterness of this aqueous extract of *Houttuynia cordata*, including organic extraction, roasting the herb, or bleach. Many groups have reported using pressurized organic solvent extraction to reduce the bitterness of hops.

According to particular aspects and as described in this Example, to reduce the bitterness and increase the palatability of the *Houttuynia cordata* extract, the *Houttuynia cordata* extract is subjected to further separation using centrifugation and heat-distillation. According to further aspects, it is this last step of heat-distillation that removes the majority of the bitterness and unpleasant taste associated with the *Houttuynia cordata* extract, and modifies it to a palatable extract suitable for oral administration. According to yet further aspects, this heat-distillation process not only provides for separation of the unpalatable and palatable portions, but also allows for separation of the anti-nausea and/or anti-emetic activity from the largely unpalatable portion. According to still further aspects, this heat-distillation process purifies and concentrates the anti-nausea and/or anti-emetic activity. According to certain aspects, the separation and/or removal of the bitterness from the aqueous extract and the separated aqueous extract using heat-distillation can be separation and/or can be a loss of the bitter flavor.

The commercially-available herb *Houttuynia cordata* Thunb was either grown locally or purchased from a Chinese herb shop (e.g., Star Import, Honolulu) for use in the following embodiments:

D-YXC-1 Process:

The following steps (1)-(7) comprise a process embodiment for producing D-YXC-1, suitable for oral delivery and in particular embodiments, for inhalation:

(1) Aqueous extraction. Fresh *Houttuynia cordata* or previously frozen *Houttuynia cordata* was immersed in a container of boiling water (454 g dried herb/5 L $H_2O$) and briefly stirred to disperse the herb. The container was immediately removed from the heat source, covered with a lid and the contents allowed to "steep" for about 8-10 hours (e.g., overnight) to produce an aqueous extract;

(2) Crude Filtration. The "aqueous extract" of step (1) was decanted from its container and gravity filtered through one or more layers of standard cheese cloth to produce a filtered aqueous extract. The steeped herb was compressed (e.g., by hand or mechanical means) to remove as much liquid as possible for filtration;

(3) Low-speed centrifugation. The "filtered aqueous extract" of step (2) was centrifuged (this is a preferred step to remove larger cellular debris, which facilitates subsequent steps) at 3,500×G for 10 minutes at ambient temperature to produce a pellet, and an aqueous supernatant fraction;

(4) Second Crude filtration. The "aqueous supernatant fraction" of step (3) was decanted from the centrifugation tubes and gravity filtered through one or more layers of standard cheese cloth to produce a filtered aqueous supernatant fraction;

(5) Distillation. The "filtered aqueous supernatant" fraction from step (4) was transferred to a standard distillation apparatus equipped with a temperature-controlled heating jacket (set at a temperature of slightly greater than about 100° C.) and a water-cooled condensation arm; Distillation was allowed to proceed until the volume of distillate was about half (i.e., about 2 L) that of the initial "filtered aqueous supernatant" volume to produce a distillate fraction (100 mL increments (from a 1000 mL sample) were tested for the presence of the bitter taste (described herein); after approximately 600 mL the bitter taste was detected no longer);

(6) Adjustment of pH and ionic strength. Phosphate buffer (of about pH 7) was added to the "distillate" fraction of step (5) to a final concentration of about 1 mM (e.g., by adding 1 ml of 1M phosphate buffer per liter of "distillate"). Solid sodium chloride was then added to a final concentration of about 0.85% (wt./volume) (e.g., to a concentration corresponding to "standard physiological saline") to produce a pH- and ionic strength-adjusted distillate fraction, D-YXC-1;

(7) Filter sterilization. The "D-YXC-1" fraction of step (6) was filter sterilized by passage through a 0.2μ membrane filter (Millipore) to produce sterile D-YXC-1, suitable for oral delivery or delivery by injection or inhalation; and (8) Storage. D-YXC-1, produced in accordance with steps (1)-(7) of the D-YXC-1 process, retained stable therapeutic activity when stored either at ambient temperature or refrigerated (e.g., 4° C.) in sterilized containers. In particular aspects, D-YXC-1 was dried or lyophilized, stored at ambient temperature and reconstituted (e.g., with sterile water or other suitable vehicle) prior to use.

D-YXC-2 Process:

The following steps (1)-(2) comprise a process embodiment for producing D-YXC-2, suitable for oral delivery, or for delivery by inhalation:

(1) Preparation of a distillate fraction. Steps (1)-(5) of the above-identified D-YXC-1 process were followed to produce a distillate fraction, D-YXC-2;

(2) Filter sterilization. The "D-YXC-2" fraction of step (1) was filter sterilized according to step (7) of the above-identified D-YXC-1 process to produce sterile D-YXC-2 suitable for oral delivery or delivery by inhalation (i.e., aerosol); and (3) Storage. D-YXC-2, produced in accordance with steps (1)-(2) of the D-YXC-2 process retained stable therapeutic activity when stored either at ambient temperature or refrigerated (e.g., 4° C.) in sterilized containers. In particular aspects, D-YXC-2 was dried or lyophilized, stored at ambient temperature and reconstituted (e.g., with sterile water or other suitable vehicle) prior to use.

General Considerations for Practice of the Above-Identified D-YXC-1 and 2 Process Embodiments:

The above-identified steps comprising embodiments of the D-YXC-1 (steps 1-7) and D-YXC-2 (steps 1-2) processes may be practiced with various modifications, including but not limited to those outlined below, that are within the scope of the present invention, and with alternatives or substitutions that will be recognized by those of ordinary skill in the art as being equivalent to those used herein to produce embodiments of D-YXC-1 and D-YXC-2.

The D-YXC-1 and D-YXC-2 embodiments of the present invention comprise aqueous extraction steps. Variations in the precise temperature and duration of the aqueous extraction steps are encompassed by the present invention. The fresh herb can optionally be cut-up or ground (e.g., blended in a commercial blender or grinder) to increase the extractable surface area. Additionally, the fresh herb can be frozen and thawed prior to blending to optimize the extraction process. Preferably, a ratio of about 250 gm dried plant tissue to about 1 L water is used, but the ratio is not critical and the amount of plant tissue may vary from about 100 to about 300 gm/L.

The above-described D-YXC-1 and D-YXC-2 embodiments comprise distillation steps. Variations in the nature of the heat source (e.g., temperature-controlled heating jacket, or steam distillation apparatus) or the precise temperature of heat source (within a range from about 100° C. to 102° C., where 100° C. represents the boiling point of water at sea level) and duration of the distillation steps will vary according to the precise distillation temperature and device used, and are within the scope of the present invention. Preferably, distillation is controlled by heating the solution at a temperature(s) within a range from 80° C. to 120° C. More preferably, distillation is controlled by heating the solution at a temperature(s) within a range from 90° C. to 110° C. Even more preferably, distillation is controlled by heating the solution at a temperature(s) within a range from 95° C. to 105° C. Most preferably, distillation is controlled by heating the solution at the lowest possible temperature that will still permit the solution to boil.

The above-described D-YXC-1 and D-YXC-2 embodiments comprise filtration steps. Variation in the mode of filtration or associated manipulations are within the scope of the present invention. For example, the "aqueous extract" or "aqueous supernatant fractions" corresponding to steps (1) and (3), respectively, of the D-YXC-1 process can optionally be frozen to induce precipitation (e.g., of unwanted starchy material) prior to the corresponding filtration and/or centrifugation steps (2), (3) and (4). Optionally, fresh *Houttuynia cordata* plants can be frozen for any length of time prior to processing. Optionally, this pre-freezing of fresh plants prior to processing (pre-boiling) assists in breaking and weakening of cell membranes and/or subsequent separation of materials (e.g., starch).

Preferably, the DYXC-1 and 2 distillate compositions are standardized (spectrophotometrically) at a value of about 200 mg (dried herb wt equivalents)/ml. Dosages are discussed herein above under "Dose Determinations."

In particular aspects, D-YXC-1 and 2 were dried or lyophilized, stored at ambient temperature and reconstituted (e.g., with sterile water or other suitable vehicle) prior to use.

According to particular aspects, the active anti-emetic factor contained within the extract is a very small molecule having a molecular weight of less than 1000 daltons, which is adsorbed rapidly and can block the vagus nerve from receiving stimuli due to pain, motion, infection, or as a complication attributed to certain medications (e.g., chemotherapy medications). According to additional aspects, treating nausea with *Houttuynia cordata* extract results in blockage of these stimuli and thus without further stimulation, the vomiting center in the region of the medulla oblongata is sedated.

According to further aspects, DYXC has substantial utility to treat nausea in both humans and animals caused by illnesses, infections, or other treatments, and in particular embodiments is used in combination with one or more of the inventive Thyex compositions, plus or minus standard chemotherapy drugs, for the treatment of cancer.

According to particular aspects, D-YXC has substantial utility to treat nausea in both humans and animals caused by illnesses, infections, or other treatments, and in particular embodiments is used in combination with one or more of the inventive Thyex compositions. According to particular aspects, D-YXC has substantial utility to treat nausea in both humans and animals caused by illnesses, infections, or other treatments, and in particular embodiments is used in combination with one or more of the inventive Thyex compositions.

EXAMPLE 17

*Houttuynia cordata* Extracts Had Substantial Use as an Anti-Nausea/Anti-Emetic Therapeutic in Mammals

*Houttuynia cordata* extracts (DYXC) were prepared as disclosed in Example 10. A canine patient presented with an acute gum lesion due to pyorrhea. In addition, blood samples indicated that the animal had a systemic infection and had acute dehydration due to frequently vomiting. A treatment regime of 2 cc of DYXC placed directly into mouth of the animal every hour was begun. The intense vomiting halted almost immediately and within three days the canine began to eat and drink normally. After seven days of treatment the acute gum lesion due to pyorrhea healed completely. The anti-nausea properties of the *Houttuynia cordata* extracts (DYXC) was confirmed through a number of other cases.

EXAMPLE 18

*Houttuynia cordata* Extracts Had Substantial Use as an Anti-Emetic Therapeutic in Humans

*Houttuynia cordata* extracts were prepared as disclosed in Example 10. A female human patient presented with severe nausea due to the chemotherapy treatment from her stomach cancer. The subject reported that the nausea was very taxing. About 30 cc of the *Houttuynia cordata* extract (DYXC) was administered to the subject (orally) as needed for treating the nausea. The subject reported rapid abatement of nausea.

Likewise, a male human cancer patient being treated with chemotherapy presented with severe nausea. About 30 cc of the *Houttuynia cordata* extract (DYXC) was administered to the subject (orally) as needed for treating the nausea. The subject reported rapid and substantial abatement of nausea within a few minutes after administration.

EXAMPLE 19

*Houttuynia cordata* Extracts has Substantial Use as Anti-Nausea/Anti-Emetic Therapeutics Animals (e.g., Vertebrates, Mammals, Etc.)

*Houttuynia cordata* extracts are prepared, for example, as disclosed in Example 10. According to certain aspects, the heat distilled extracts of *Houttuynia cordata* have substantial use in relieving nausea and/or vomiting. This nausea and/or vomiting can be due to any condition including, but not limited to pregnancy, motion sickness, gastrointestinal obstruction, peptic ulcer, drug toxicity, myocardial infarction, renal failure, and hepatitis. In addition, nausea and/or vomiting can follow the administration of many drugs particularly cancer chemotherapeutic agents. According to certain aspects, subjects presenting with nausea and/or vomiting find that these symptoms quickly abate upon treatment with the *Houttuynia cordata* heat distilled extracts (DYXC).

EXAMPLE 20

*Houttuynia cordata* Extracts are Further Fractionated to Identify the Anti-Nausea Agent As shown in Example 10, *Houttuynia cordata* extracts can be fractionated into portions that contain anti-nausea and/or anti-emetic activity. According to certain aspects, the heat distilled fraction (as disclosed in Example 10) can be further fractionated using separation techniques well known in the art (e.g., fractional distillation, centrifugation, chromatography, crystallization, electrophoresis, evaporation, extraction, flotation, flocculation, precipitation, and column chromatography). The further separated fractions can be screened for anti-nausea and/or anti-emetic activity as described herein. In addition and according to particular aspects, the further separated fractions can be screened for anti-nausea and/or anti-emetic activity using methods well known in the art (e.g., using test frogs and/or chicks). For example, researchers have used frogs and chicks that were induced to vomit by emetic agents to test anti-nausea and/or anti-emetic agents for years (Khan, R. A., et al., 2005 "Preliminary Screening of Methanol and Butanol Extracts of *Tamarindus indica* for Anti-Emetic Activity," J. Basic and Applied Sciences, Vol. 1, No. 2; Kawai, T., et al., 1994 "Anti-emetic principles of Magnolia obovata and Zingiber officinale." Planta Med. 60: 17-20; Kinoshita, K., et al., 1996. "Anti-emetic principles of *Inula linariaefolia* flowers and Forsythia suspense fruits", Phytomedicine 3: 51-58; Tai, T., et al., 1995. "Anti-emetic principles of *Poria cocos*." Plants Med. 61: 493-590; Akita, Y., et al., 1998. "New assay method for surveying anti-emetic compounds from natural sources." Nat Prod Sci 4(2): 72-77; Yang, Y., et al., 1999. "Anti-emetic principles of *Pogostemon cabin* (blanco) benth." Phytomedicine 6(2):89-93; all of which are incorporated herein by reference in their entireties and particularly for their teachings relating to assays and screening methods for detecting/characterizing anti-nausea/anti-emetic agents). Given the presently disclosed novel anti-nausea/anti-emetic activity of the *Houttuynia cordata* extracts, coupled with the knowledge and skill in the art with respect to standard fractionation and purification methods, particular aspects of the invention provide not only for the heat-distilled *Houttuynia cordata* extract (e.g., of Example 10), but for routine fractionation, concentration, and/or purification of the anti-nausea/anti-emetic activity to provide for fractionated, concentrated, and/or purified derivative fractions of the heat-distilled *Houttuynia cordata* extract (e.g., of Example 10).

EXAMPLE 21

Treatment of Allergy and Autoimmune Disorders Using the Inventive Thyex Compositions In further aspects, the inventive Thyex compositions are used to treat individuals with allergy and autoimmune disorders (lichen sclerosis set atrophicus, rheumatoid arthritis, psoriasis, progressive systematic scleroderma, lupus, and juvenile diabetes).

Without being bound by theory, the mechanism may comprise stimulation of suppressor T cells, which direct B cells producing the allergy antibodies to stop continued activity and control of reactive T cells.

The invention claimed is:

1. A method for treating arthritis characterized by joint inflammation and swelling, comprising administering to a mammalian subject in need thereof a therapeutically effective amount of a heat-treated, fractionated thymus extract composition comprising thymus proteins or polypeptides having molecular weights ranging from 3.5 kDa to 30 kDa, including from 5 kDa to 14 kDa, and lacking proteins or polypeptides having molecular weights less than about 3.5 kDa and greater than about 30 kDa, the therapeutically effective amount being sufficient to reduce joint inflammation, pain and swelling, wherein a method for treating arthritis characterized by joint inflammation and swelling is afforded.

2. The method of claim 1, wherein the mammal is a human.

3. The method of claim 1, wherein the arthritis comprises one or more selected from the group consisting of osteoarthritis, rheumatoid arthritis, psoriatic arthritis and inflammation resulting from any of these conditions.

4. The method of claim 1, wherein the arthritis comprises rheumatoid arthritis (RA) and/or inflammation resulting therefrom.

5. The method of claim 1, further comprising adjunctively administering a therapeutically effective amount of a macrophage stimulating agent in combination with administration of the thymus extract composition.

6. The method of claim 5, wherein the macrophage stimulating agent comprises at least one selected from the group consisting of: a polysaccharide, a beta glucan comprising a beta 1,3 glucan linkage, a beta glucan comprising a beta 1,4 glucan linkage and a beta glucan comprising a beta 1,6 glucan linkage.

7. The method of claim 6, wherein the beta glucan comprises a beta 1,3 glucan linkage.

8. The method of claim 1, further comprising adjunctively administering a therapeutically effective amount of at least one other anti-inflammation agent or treatment in combination with administration of the thymus extract composition.

9. The method of claim 8, wherein the anti-inflammatory agent is at least one selected from the group consisting of: a glucocorticoids, hydrocortisone (cortisol), cortisone acetate, prednisone, prednisolone, methylprednisolone, dexamethasone, betamethasone, triamcinolone, beclometasone, non-steroidal anti-inflammatory drugs (NSAIDs), a COX-2 inhibitors, diclofenac, etoricoxib, indomethacin, ketoprofen, naproxen and sulindac.

10. The method of claim 9, wherein the anti-inflammatory agent comprises a glucocorticoid.

11. The method of claim 1, further comprising adjunctively administering a therapeutically effective amount of an extract of *Houttuynia cordata* sufficient to reduce nausea in combination with administration of the thymus extract composition.

12. The method of claim 1, wherein administering the heat-treated, fractionated thymus extract composition limits infiltration of immune cells into the joints of the subject.

13. The method of claim 12, further comprising administering an anti-inflammation agent in combination with administration of the thymus extract composition.

14. The method of claim 1, wherein the heat-treated, fractionated thymus extract composition is prepared by a method comprising:
homogenizing thymus tissue with aqueous homogenization fluid to produce an aqueous thymus homogenate;
removing tissue debris from the aqueous thymus homogenate to produce a primary supernatant;
heat denaturing the primary supernatant, and clarifying the denatured primary supernatant by use of at least one of low-speed centrifugation and filtration, to produce a clarified supernatant; and
separating molecules having molecular weights less than about 3.5 kDa and greater than about 30 kDa from the clarified supernatant, wherein a heat-treated, fractionated thymus extract composition comprising thymus proteins or polypeptides having molecular weights ranging from 3.5 kDa to 30 kDa, including from 5 kDa to 14 kDa, and lacking proteins or polypeptides having molecular weights less than about 3.5 kDa and greater than about 30 kDa is provided.

15. The method of claim 14, wherein, in the method for preparing the heat-treated, fractionated thymus extract composition, the initial ratio of thymus tissue to aqueous homogenization fluid is about 350 g wet weight of thymus tissue to about 0.7 L of homogenization fluid.

16. The method of claim 14, wherein, in the method for preparing the heat-treated, fractionated thymus extract composition, no steps involving exogenously added protease digestion, or extraction with organic solvents are used.

17. The method of claim 1, wherein the heat-treated, fractionated thymus extract composition is prepared by a method comprising:
homogenizing thymus tissue with aqueous homogenization fluid to produce an aqueous thymus homogenate;
removing tissue debris from the aqueous thymus homogenate to produce a primary supernatant;
heat denaturing the primary supernatant, and clarifying the denatured primary supernatant by use of at least one of low-speed centrifugation and filtration to produce an intermediate clarified supernatant;
concentrating the intermediate clarified supernatant to produce a concentrated intermediate fraction; and
separating molecules having molecular weights less than about 3.5 kDa and greater than about 30 kDa from the concentrated intermediate fraction, wherein a heat-treated, fractionated thymus extract composition comprising thymus proteins or polypeptides having molecular weights ranging from 3.5 kDa to 30 kDa, including from 5 kDa to 14 kDa, and lacking proteins or polypeptides having molecular weights less than about 3.5 kDa and greater than about 30 kDa is provided.

18. The method of claim 17, wherein, in the method for preparing the heat-treated, fractionated thymus extract composition, the initial ratio of thymus tissue to aqueous homogenization fluid is about 350 g wet weight of thymus tissue to about 0.7 L of homogenization fluid.

* * * * *